(12) United States Patent
Goldberg et al.

(10) Patent No.: US 7,511,018 B2
(45) Date of Patent: Mar. 31, 2009

(54) JUVENILE HEMOCHROMATOSIS GENE (HFE2A) CLEAVAGE PRODUCTS AND USES THEREOF

(75) Inventors: Yigal P. Goldberg, Vancouver (CA); Rajender K. Kamboj, Burnaby (CA)

(73) Assignee: Xenon Pharmaceuticals, Inc., Burnaby (CA)

( * ) Notice: Subject to any disclaimer, the term of this patent is extended or adjusted under 35 U.S.C. 154(b) by 0 days.

(21) Appl. No.: 11/197,710

(22) Filed: Aug. 4, 2005

(65) Prior Publication Data
US 2006/0073497 A1 Apr. 6, 2006

Related U.S. Application Data

(63) Continuation-in-part of application No. PCT/CA2004/000522, filed on Apr. 8, 2004.

(60) Provisional application No. 60/462,867, filed on Apr. 15, 2003, provisional application No. 60/488,607, filed on Jul. 18, 2003, provisional application No. 60/498,458, filed on Aug. 28, 2003.

(51) Int. Cl.
*A61K 38/00* (2006.01)
*C07K 1/00* (2006.01)
*C12N 9/00* (2006.01)

(52) U.S. Cl. .................. 514/12; 530/350; 435/183
(58) Field of Classification Search .................. 435/183; 530/350; 514/12
See application file for complete search history.

(56) References Cited

U.S. PATENT DOCUMENTS 6,943,241 B2 * 9/2005 Isogai et al. ................ 536/23.1
2004/0102376 A1 5/2004 Mueller et al.

FOREIGN PATENT DOCUMENTS

| WO | WO 96/13518 | | 5/1996 |
|---|---|---|---|
| WO | WO 00/73801 | | 12/2000 |
| WO | 02/051438 | * | 7/2002 |
| WO | 51438 | * | 7/2002 |
| WO | WO 02/51438 | | 7/2002 |
| WO | 02/074961 | * | 9/2002 |
| WO | WO 2004/092405 | | 10/2004 |
| WO | 200274961 | * | 9/2006 |

OTHER PUBLICATIONS

Hopkins et al., PNAS USA, 99(26), 2002, 16899-16903.*
Pender et al., J. Med. Chem. vol. 44, pp. 36-46 (2001).
Afanassiev et al., Mutation Research, 464(2):297-308 (2000).
Goldberg et al., Amer. J. Human Genetics, 73(5):205 (2003)—Abstract.
Gonzalez et al. Current Opinion in Biotechnology, 9(6):624-631 (1998).
Hertzberg et al., Current Opinion in Chemical Biology, 4(4):445-451 (2000).
Koller et al., Treands in Pharmacological Sciences, 21(4):142-148 (2000).
Taupin et al., J. Immunological Methods, 256:77-87 (2001).
Mattheakis et al., Chemistry and Biology, 6(11):835-844 (1999).

* cited by examiner

*Primary Examiner*—Maryam Monshipouri
(74) *Attorney, Agent, or Firm*—Elliot M. Olstein; Alan J. Grant

(57) ABSTRACT

Isolated fragments of the HFE2A protein able to bind and modulate HFE2A and other proteins, such as hepcidin, involved in the iron metabolism pathway are disclosed, such fragments being of molecular weight of approximately 7 kDa to 43 kDa. Also disclosed are corresponding isolated polynucleotides encoding the fragments of the HFE2A protein. The invention includes derivatives and analogs of the polypeptide fragments of HFE2A, along with compositions of these, that are functionally active, i.e., capable of interacting with the HFE2A, as well as methods of production of the HFE2A cleavage products, derivatives and analogs, e.g., by recombinant means. Methods for identifying modulators of HFE2A are provided. Also taught are methods of diagnosing an animal afflicted with or at risk of developing a disease of iron metabolism. Methods for treating and/or preventing a disorder in animals comprising administering a therapeutically effective amount of an HFE2A modulator are provided.

18 Claims, 13 Drawing Sheets

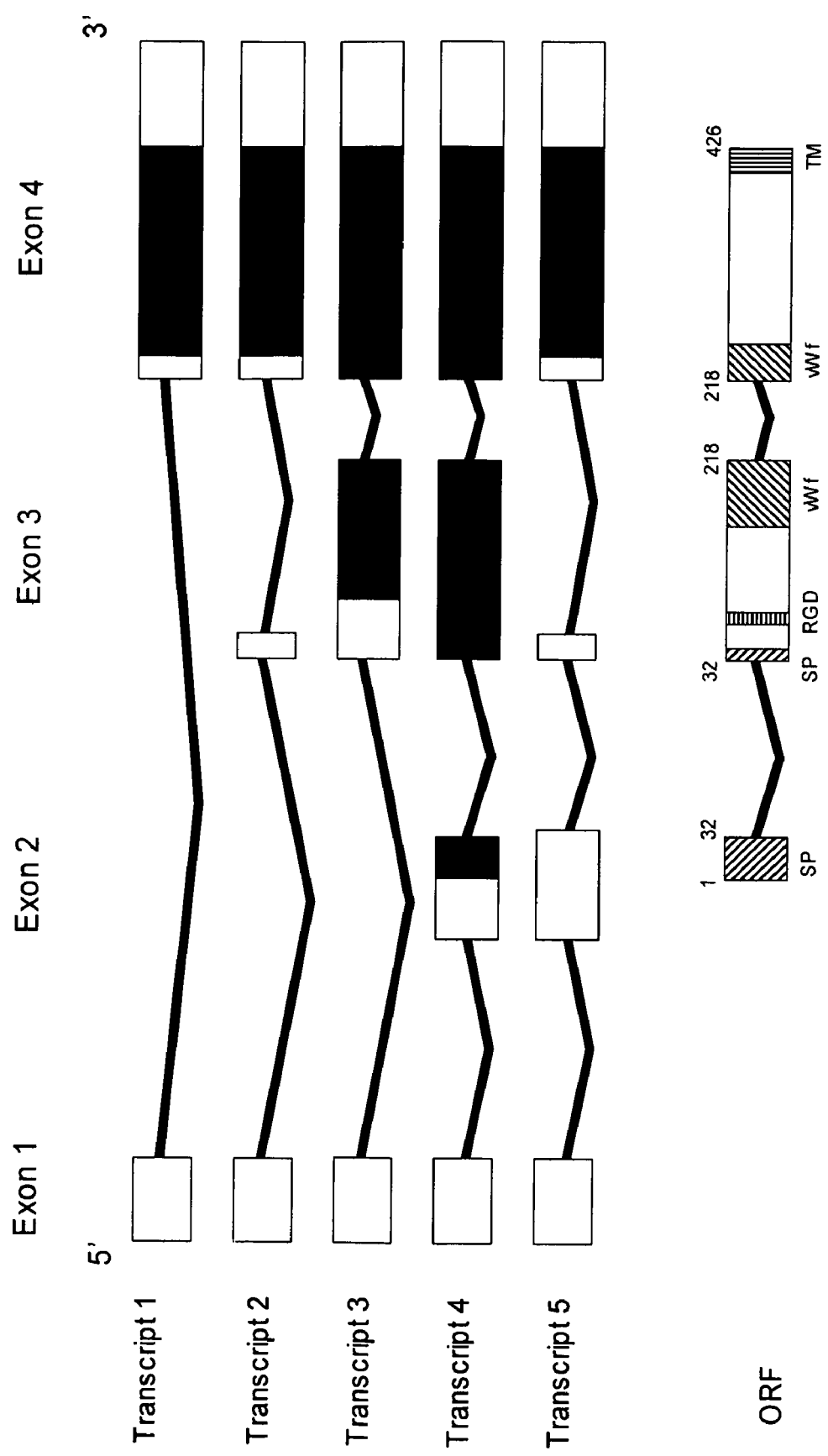

Fig 2

| | | | |
|---|---|---|---|
| Human | : MGEFQGSPSRSSHGSEPT—LSTITITI—LIILG—GHAHECKILRCNAEYVSSTLSIRGGSSGAIRCCGGGGPGCGVSGGIICPAIPSYALCT | : 90 |
| Chicken_RGM | : M—RCAGSTAIGIFQIICIFPVFIICTFPEWTSPCKILKCNSEFWAAT————SGSH-HI————GAEETPEFCTALRAYAHCI | : 68 |

| | | | |
|---|---|---|---|
| Human | : RRTARTCRGILAFHSAVHGIEDLMICHNCSRQGPTAPPEERGPAIPGAGSGLF—APDPCYEGFSRLHGPPECFIHCASFGEPHVRSFHHF | : 182 |
| Chicken_RGM | : RRTARICRGELAYHSAVHGIDDIMVCHNCSKDGPTSQPFIRTLF—PGDSCERSDSPEICHYEKSFHK—HSAAPNYTHCGIFGEPHLRTFLTF | : 159 |

| | | | |
|---|---|---|---|
| Human | : HTCRVQGAWPLIENEFLFVQATSSFVAIGANATAIRKLTIIFKNKQECIDCKVYQAEVDNIPVAFEDGSINGGDREGGSSLSIQTANEGNHVEI | : 276 |
| Chicken_RGM | : CTCKVQGAWELIDNNYLINVQVTNTPVLFGSSATATSKITIFKSFQECVECKVYQAEMDEIPAAFADGSKNGGDKHCANSLKITEKVSGCHIEI | : 253 |

| | | | |
|---|---|---|---|
| Human | : CAAYICTIIIRCTAGCISFSIKVAEDVANAFSAE—QEIQICLVGGCPPSC—RLSRSE—PNRP—C—AITICTARPICKEG | : 350 |
| Chicken_RGM | : CAKYICTTIVVRQVGRYITFAVRMPEEVVNAVEDRDSGCLYICIRGCFINCCTECTERLACAAEGRARRKGFSIPAPPEAFTVESATAKCREK | : 347 |

| | | | |
|---|---|---|---|
| Human | : LPVEDAYFHSCVFDVIISGDPNFTVAAQAALEDARAFTIPDIEKLHLF—PSLAGVFLSSATLIAPLISGLFVLWICIQ | : 426 |
| Chicken_RGM | : IPVEDLLYFQSCVELLLTLGDVNFMLAAYYAFEDVKMLHSNKCKLHLYERTRALAFGNAAPSEHPWAIPAIWVALLS—LSCCWIGLI | : 432 |

```
                    *                     *                    *                    *
LOC148738   : CASFGDPHVRSFH----HHFHTCRVQGAWPLLDNDELFVQATSSPMALGA :  46
gnl|CDD|192 : CSVSGDGHYTEDGRKYTFPGNCTYVLAQDCTSEPSESVLKNVN--GG :  48

*                     *                    *
LOC148738   : NATATRKLTIIEKNMQECIDQKVYQAEVD----NLPVAEFDGSIN :  87
gnl|CDD|192 : DATCLKSVKVELNDIEIELKDGGKVTVNGQKVSLPYKTSDGSIR :  93
                         220                  240                260
```

Fig 4F

Furin Cleavage → SERNRRGAITID

Figure 6 - 1

```
  1      ATGGGGGAGCCAGGCCAGTCCCCTAGTCCCCAGGTCCTCCCATGGCAGTCCCCAACTCTA
  1     -M---G---E---P---G---Q---S---P---S---P---R---S---S---H---G---S---P---P---T---L-

61      AGCACTCTCACTCTCCTGCTGCTCCTCTGTGGACATGCTCATTCTCAATGCAAGATCCTC
 21     -S---T---L---T---L---L---L---L---L---C---G---H---A---H---S---Q---C---K---I---L-
                                                                              π
121      CGCTGCAATGCTGAGTACGTATCGTCCACTCTGAGCCTTAGAGGTGGGGTTCATCAGGA
 41     -R---C---N---A---E---Y---V---S---S---T---L---S---L---R---G---G---S---S---G-

181      GCACTTCGAGGAGGAGGAGGAGGCCGGGGTGGAGGGGTGGGCTCTGGCGGCCTCTGT
 61     -A---L---R---G---G---G---G---G---R---G---G---G---V---G---S---G---G---L---C-

241      CGAGCCCTCCGCTCCTATGCGCTCTGCACTCGGCGCACCGCCACTGCCGCGGGAC
 81     -R---A---L---R---S---Y---A---L---C---T---R---R---T---C---R---T---C---R---G---D--●

301      CTCGCCTTCCATTCGGCGGTACATGCATCGAAGACCTGATGATCCAGCACACAACTGCTCC
101     -L---A---F---H---S---A---V---H---G---I---I---E---D---L---M---I---Q---H---N---C---S--●

361      CGCCAGGGCCCTACAGCCCCTACAGCCCCCTACAGCCCCCTTCCAGGCGCGGCTCC
121     -R---Q---G---P---T---A---P---P---P---P---R---G---P---A---L---P---G---A---G---S--●

421      GGCCTCCCTGCCCCGACCCTTGTGACTATGAAGGCCGGTTTTCCCGGCTGCATGGTCGT
141     -G---L---P---A---P---D---P---C---D---Y---E---G---R---F---S---R---L---H---G---R-

481      CCCCCGGGGTTCTTGCATTGCGCTTCCTTCGGGGACCCCATGTGCGCAGCTTCCACCAT
161     -P---P---G---F---L---H---C---A---S---F---G---D---P---H---V---R---S---F---H---H-

541      CACTTTCACACATGCCGTGTCCAAGGAGCTTGGCCTCTACTGATAATGACTTCCTCTTT
181     -H---F---H---T---C---R---V---Q---G---A---W---P---L---L---D---N---D---F---L---F-

601      GTCCAAGCCACCAGCTCCCCCATGGCGTTGGGGGCCAACGCCTACCGCCACCCGGAAGCTC
201     -V---Q---A---T---S---S---P---M---A---L---G---A---N---A---T---A---T---R---K---L-

661      ACCATCATATATTAAGAACATGCAGGAATGCATTGATCAGGAAGGTGTATCAGGCTGAGGTG
221     -T---I---I---F---K---N---M---Q---E---C---I---D---Q---K---V---Y---Q---A---E---V-
```

Figure 6 - 2

```
 721  GATAATCTTCCTGTAGCCTTTGAAGATGGTTCTATCAATGGAGGTGACCGACCTGGGGA
 241  -D---N---L---P---V---A---F---E---D---G---S---I---N---G---G---D---R---P---G---G-

781  TCCAGTTTGTCGATTCAAACTGCTAACCCTGGGAACCATGTGGAGATCCAAGCTGCCTAC
 261  -S---S---L---S---I---Q---T---A---N---P---G---N---H---V---E---I---Q---A---A---Y-

841  ATTGGCACACAACTATAATCATTCGGCAGACAGCTGGGCAGCTCTCCTTCTCCATCAAGTA
 281  -I---G---T---T---I---I---R---Q---T---A---G---Q---L---S---F---S---I---K---V-

901  GCAGAGGATGTGGCCATGGCCTTCTCAGCTGAACAGGACCTGCAGCTCTGTGTTGGGGGG
 301  -A---E---D---V---A---M---A---F---S---A---E---Q---D---L---Q---L---C---V---G---G-

961  TGCCCCTCCAAGTCAGCGACTCTCTGATCAGAGCCAATCGTCGGGGAGCTATAACCATT
 321  -C---P---P---S---Q---R---L---S---R---S---E---R---N---R---G---A---I---T---I-

1021  GATACTGCCAGACGGCTGTGCAAGGAAGGGCTTCCAGTGGAAGATGCTTACTTCCATTCC
 341  -D---T---A---R---R---L---C---K---E---G---L---P---V---E---D---A---Y---F---H---S-

1081  TGTGTCTTTGATGTTTAATTTCTGGTGATCCCAACTTTACCGTGGCAGCTCAGGCAGCA
 361  -C---V---F---D---V---L---I---S---G---D---P---N---F---T---V---A---A---Q---A---A-

1141  CTGGAGGATGCCCGAGCCTTCCTGCCAGACTTAGAGAAGCTGCATCTCTTCCCCTCAGAT
 381  -L---E---D---A---R---A---F---L---P---D---L---E---K---L---H---L---F---P---S---D-

1201  GCTGGGGTTCCTCTTTCCTCAGCAACCCTCTTAGCTCCACTCCTCTTTCTGGGCTCTTTGTT
 401  -A---G---V---P---L---S---S---A---T---L---A---P---L---L---S---G---L---F---V-

1261  CTGTGGCTTTGCATTCAGTAAGGGACCATCAGTCCCATTACTAGTTTGGAAATGATTTG
 421  -L---W---L---C---I---Q---*
```

US 7,511,018 B2

JUVENILE HEMOCHROMATOSIS GENE (HFE2A) CLEAVAGE PRODUCTS AND USES THEREOF

This application is a continuation-in-part of International Application PCT/CA2004/000522, filed 8 Apr. 2004, now U.S. National Phase application Ser. No. 10/552,158, pending which claims priority of U.S. provisional applications Ser. No. 60/462,867, filed 15 Apr. 2003, Ser. No. U.S. 60/488,607, filed 18 Jul. 2003, and Ser. No. 60/498,458, filed 28 Aug. 2003, the disclosures of all of which are hereby incorporated by reference in their entirety.

FIELD OF THE INVENTION

The present invention is directed generally to the juvenile hemochromatosis gene (HFE2A) related to diseases of iron metabolism, more particularly, to cleavage products of HFE2A and their role in regulating diseases of iron metabolism, including diagnostic, screening and therapeutic methods.

BACKGROUND OF THE INVENTION

Genetic, molecular and clinical studies have lead to the identification of a medical disorder called juvenile hemochromatosis (sometimes called "JH" or "juvenile haemochromatosis"), which is also known as hemochromatosis type 2 ("HFE2").

In some families juvenile hemochromatosis shows linkage to chromosome 1q21, whereas in others it is caused by mutation in the gene encoding hepcidin antimicrobial peptide, which maps to chromosome 19q13. The two forms of juvenile hemochromatosis (HFE2) are tentatively designated HFE2A and HFE2B, respectively. The present invention relates to HFE2A gene and protein, (the JH gene linked to chromosome 1q21), and more specifically to the cleavage products of HFE2A The intact (i.e. full-length) HFE2A has been implicated in diseases of iron metabolism (PCT Patent Publication No. WO 04/092405). Specific fragments of HFE2A, i.e., cleavage products, have not, previously, been explicitly identified and the role they may play in the regulation of diseases of iron metabolism has remained obscured.

Such fragments are a soluble form of HFE2A and the present invention for the first time offers these as a critical regulator of iron metabolism. Thus, an object of the present invention is to provide cleavage products of the HFE2A, thereby facilitating development of more potent agents for treating and diagnosing iron overload diseases and iron deficiency diseases. Moreover, such identification enables a better understanding of the operation of the HFE2A and its cleavage products in the development and regulation of diseases of iron metabolism, in general, and all forms of iron overload in particular hemochromatosis, as well as Anemia of Inflammation, in particular.

BRIEF SUMMARY OF THE INVENTION

The invention relates to the disorder juvenile hemochromatosis (hemochromatosis type 2A, or HFE2A), which is caused by a mutation in a human gene found at 1q22 having the nucleotide sequence as set out in SEQ ID Nos. 1-9, and/or the corresponding amino acid sequences as set out in SEQ ID Nos. 10-12. The gene and the protein are referred to herein as HFE2A and also as hemojuvelin, these words referring to the gene, the gene product and the protein expressed therefrom, unless the context specifies otherwise. The gene has also been named HFE2A, by which is meant the form JH caused by the gene at 1q21. This naming protocol is not essential to the invention claimed herein.

This invention is based, in part, on the discovery that HFE2A is cleaved into fragments at putative cleavage sites found throughout the amino acid sequence. Although not intending to be limited to any particular mechanism, these fragments are able to bind and modulate HFE2A and other proteins, e.g. hepcidin, involved in the iron metabolism pathway. The HFE2A cleavage products are fragments of the full-length HFE2A released from the cell membrane due to proteolytic cleavage at these putative cleavage sites generating one or more polypeptide fragments of varying molecular weights of approximately 7 kDa to 43 kDa.

In one aspect, the present invention encompasses isolated polypeptide fragments of the HFE2A disclosed herein and as set out in SEQ ID NO: 13-31 and/or the fragments derived from the full-length HFE2A amino acid sequences as set out in SEQ ID NO: 10-12. The corresponding isolated polynucleotides encoding these fragments of the HFE2A are also encompassed by this invention.

The invention is also directed to a derivative or analog of the polypeptide fragments of HFE2A which is functionally active, i.e. capable of interacting with the HFE2A. Methods of production of the HFE2A cleavage products, derivatives and analogs, e.g. by recombinant means, are also provided.

In another aspect, the present invention relates to a method for identifying an agent that modulates HFE2A, comprising contacting a test compound with HFE2A and determining a change in HFE2A activity due to the test compound, thereby identifying a modulator of the type being sought.

In one embodiment, a method for identifying a modulator of HFE2A activity comprises contacting an HFE2A polypeptide with a test compound in the presence of a composition and under conditions conducive to cleavage of the HFE2A polypeptide by one or more component of the composition, and detecting or measuring the presence or amount of HFE2A cleavage products that result from the cleavage, in which a difference in the presence or amount of said HFE2A cleavage products compared to an HFE2A polypeptide in presence of a composition not contacted with the test compound, thereby identifying a modulator of HFE2A activity.

In another embodiment, the present invention relates to a method for identifying an agent that modulates the activity of HFE2A polynucleotide, comprising:

(a) contacting a polynucleotide encoding an HFE2A polypeptide or fragments thereof, with a test compound under conditions promoting expression of said polynucleotide; and (b) determining a change in expression as a result of said contacting;

wherein a change identifies said test compound as an agent that modulates HFE2A polynucleotide activity.

In another aspect, the present invention relates to a method for identifying an agent that modulates the level, amount or activity of an HFE2A full-length protein or an HFE2A polypeptide fragment comprising: contacting a test compound with an HFE2A full-length protein or an HFE2A polypeptide fragment and under conditions supporting an activity of said polypeptide and determining a change in said activity of said polypeptide as a result of said contacting, wherein a change in the activity identifies said test compound as an agent that modulates the level, amount or activity of an HFE2A full-length protein or an HFE2A polypeptide fragment.

In yet a further aspect, the present invention relates to a method for treating and/or preventing a disorder in animals comprising administering to an animal afflicted therewith, or at risk of developing said disorder, a therapeutically effective amount of an HFE2A modulator. In a preferred embodiment, the HFE2A modulator exhibits modulating activity in a method of the invention, most preferably wherein said agent was first identified as an HFE2A modulator using said method and was not otherwise known to have such activity.

The present invention is also directed to compositions based on the HFE2A cleavage products, derivatives, analogs, and encoding nucleic acids.

In yet a further aspect, the present invention relates to a method to diagnose an animal afflicted with or at risk of developing a disease of iron metabolism comprising:

(a) detecting the level, amount or activity of a fragment or set of fragments of an HFE2A polypeptide obtained in a sample from an individual; and (b) determining a difference in the level, amount or activity from step (a) relative to the level, amount or activity of an identical fragment or set of fragments of said HFE2A polypeptide in an individual not so afflicted or at such risk;

wherein said difference identifies said individual as being afflicted with or at risk of developing a disease of iron metabolism.

In yet another aspect, the present invention relates to a method of diagnosing an animal afflicted with or at risk of developing a disease of iron metabolism comprising:

(a) obtaining a sample from said individual and determining the level, amount or activity of a HFE2A polypeptide or fragments thereof and an iron metabolism protein (e.g. hepcidin); and (b) calculating a ratio of the level, amount or activity of the HFE2A polypeptide or the fragments relative to the iron metabolism protein, and (c) comparing the ratio to that in an individual not so afflicted or at such risk;

wherein an altered ratio identifies said individual as being afflicted with or at risk of developing a disease of iron metabolism.

Differentiation of Anemia of Chronic disease from that of true iron deficiency anemia can often be a significant challenge facing the practicing clinician. A specific test to assist in clearly differentiating these two disorders would be highly utilized and of significant value. Therefore, another aspect of the invention relates to a method for differential diagnosis between an individual having anemia of chronic diseases and having iron deficiency anemia comprising:

(a) obtaining a sample from an individual to be tested;

(b) detecting the level, amount or activity or relative ratio of a HFE2A polypeptide or fragments thereof in said sample; and (c) determining the difference in the level, amount or activity or relative ratio from step (b) relative to the level, amount or activity or relative ratio of said HFE2A polypeptide or said fragments thereof in an individual afflicted with either anemia of chronic diseases or iron deficiency anemia, wherein the level, amount or activity or relative ratio of HFE2A polypeptide or the fragments is different in each of these diseases;

thereby determining whether said individual has anemia of chronic diseases or has iron deficiency anemia.

In a yet further aspect, the present invention relates to a method to diagnose an animal afflicted with or at risk of developing a disease of iron metabolism comprising determining the nucleic acid sequence of the HFE2A gene or fragment thereof in said animal wherein a mutation or polymorphism of said gene or fragment identifies said animal as an animal afflicted with or at risk of developing a disease of iron metabolism.

Other features and advantages of the invention will be apparent from the following detailed description and from the claims.

BRIEF DESCRIPTION OF THE DRAWINGS

FIG. 1 is a schematic of HFE2A structure. The HFE2A has four exons and five transcripts. The five transcripts code for 3 proteins of 200 AA, 313 AA and 426 AA. Exon 2 was predicted by Ensembl from cDNA sequence AK098165.1. The acceptor site for Exon 2 is inferred from the genomic sequence. Exons 3a and 3b have the same acceptor site but different donor sites. Untranslated sequence is white, translated sequence is black. The transcripts are listed from shortest to longest.

FIG. 2 shows a Protein Sequence Alignment of Human HFE2A gene product and Chicken Repulsive Guidance Molecule (RGM). Human (Protein3), Chicken_RGM (Translation of NCBI: AY128507.1). A=Signal Peptide, B=RGD, C=N-Glycosylation site, D=Partial von Willebrand Type D Domain, E=GPI modification, Arrow=Possible cleavage site.

FIG. 3B shows the high degree of similarity between genes similar to HFE2A in different species.

FIG. 4D shows the identification of partial von Willebrand Type D domain (57%) using NCBI Conserved Domain Search. (LOC148738=HFE2A);

FIG. 4F shows predicted furin cleavage site representing the consensus sequence Arg-Asn-Arg-Arg[335] for the proprotein convertase furin (Molloy et al., J. Biol. Chem., 267, 16396-16402, 1992). Furin cleavage site predicted to be between R335 and G336.

FIG. 6-1 and 6-2 shows Nucleic acid and amino-acid sequence of 426 aa open-reading frame translated from Transcript4 of HFE2A (Protein3). This protein is identical to the Ensembl protein ENSP00000304614 from the predicted Ensembl transcript ENST00000306561. Box, initiating codon; triangle, potential signal peptide cleavage site; dots, RGD site; cross, predicted O-glycosylation sites (NetOGlyc 2.0 predicted); diamonds, predicted N-glycosylation sites (NetNGlyc 1.0 predicted); arrow, putative cleavage site from comparison with chicken RGM; double arrow, furin cleavage site; square, predicted GPI anchor modification site; asterix, stop codon.

DETAILED DESCRIPTION OF THE INVENTION

Figure 3A:
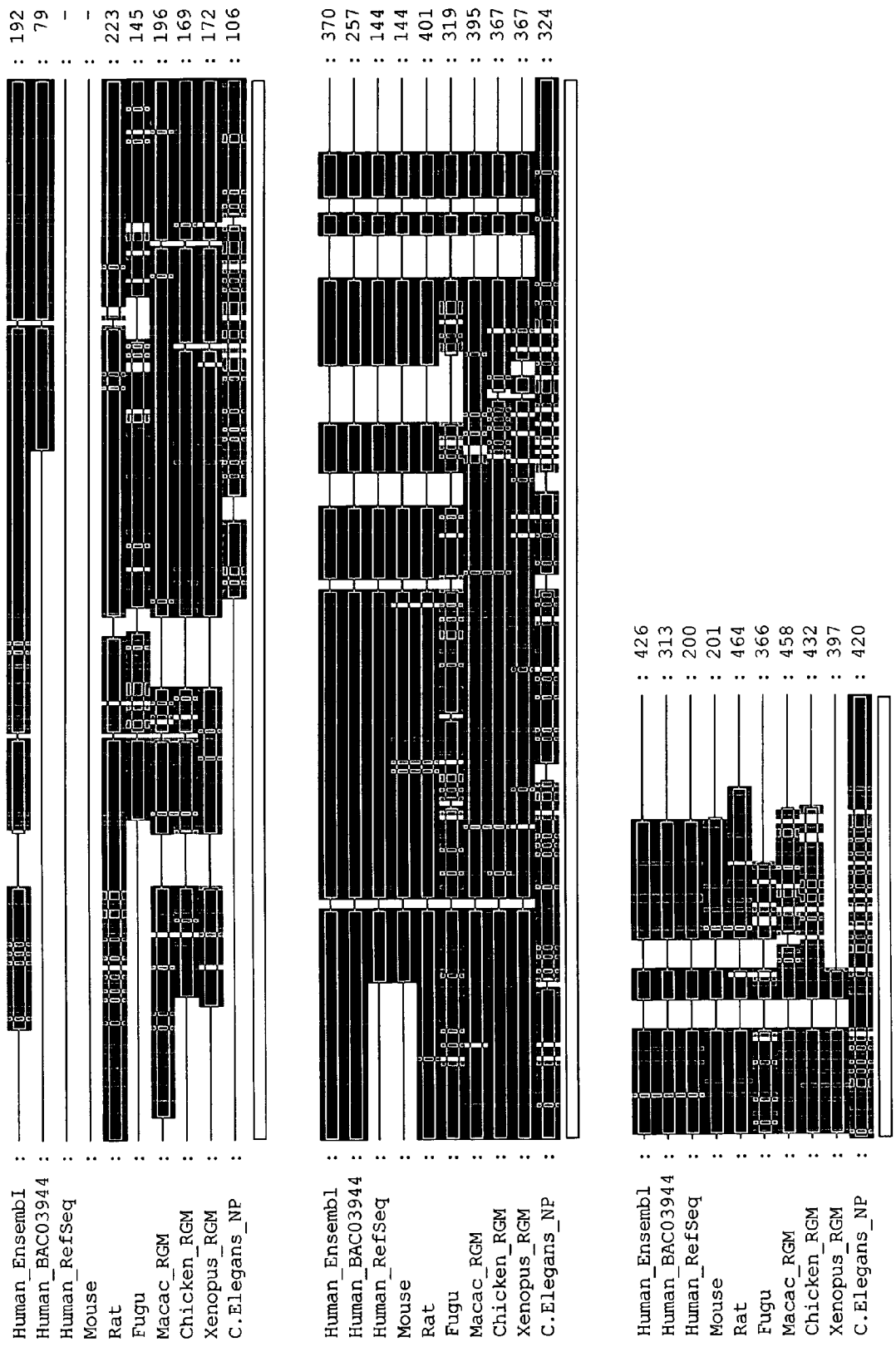
FIG. 3A shows a summary of high degree of similarity between homologs of several species.

"HFE2A" or "hemojuvelin" refers to a gene, its corresponding protein, including the polypeptide, protein and amino acid sequence, and the polymorphic, allelic, isoforms and mutants forms thereof unless otherwise stated. This gene, when mutated, results in diseases of iron metabolism, specifically juvenile hemochromatosis (hemochromatosis type 2A). The gene has also been named HFE2, by which is meant the form Juvenile Hemochromatosis caused by the gene at 1q21. However, this naming protocol is not essential to the invention claimed herein.

Human HFE2A has been identified with the full cDNA sequence first released to GenBank as GB Accession No. AY372521 dated Aug. 21, 2003. Further descriptions of HFE2A, including transcript variants can be found in GenBank under Accession Nos. BC085604, NM_213653, NM_213652, NM_202004 and NM_145277. In one aspect, the present invention is directed to cleavage products of HFE2A and their therapeutic use in individuals having symptoms of diseases of iron metabolism.

In accordance therewith, one embodiment of the present invention is directed to predicted fragments or cleavage products of the HFE2A polypeptides comprising an amino acid sequence with at least 60% identity to an amino acid sequence selected from the group consisting of SEQ ID NO: 13, 14, 15, 16, 17, 18, 19, 20, 21, 22, 23, 24, 25, 26, 27, 28, 29, 30 and 31, wherein said polypeptide has the same biological function of HFE2A or a fragment thereof. Although polypeptides with higher sequence homologies of, for example, 70%, 80%, 90%, 95% or 98% are also contemplated by this invention. Preferably, said HFE2A fragment is selected from the group consisting of SEQ ID NO: 13, 14, 15, 16, 17, 18, 19, 20, 21, 22, 23, 24, 25, 26, 27, 28, 29, 30 and 31.

In another embodiment, the present invention is directed to oligopeptides comprising at least 4, 10, 20, 30, 50, 100 or 150 contiguous amino acids of SEQ ID NO: 10, 11, or 12. In this embodiment, the oligopeptides represent HFE2A cleavage products and is believed to have the same biological function of HFE2A or a fragment thereof.

In another embodiment, the fragments of HFE2A have a molecular weight of approximately between 7 kDa and 43 kDa and exhibit biological function of HFE2A or a fragment thereof. In one embodiment, the polypeptides as set out above have the ability to modulate, e.g. agonize or antagonize, the activity of a full-length HFE2A.

The invention is also directed to derivatives or analogs of the HFE2A cleavage products which are functionally active, i.e., capable of interacting with and modulating the full length HFE2A.

In another embodiment, the polypeptide is label. In another embodiment, the polypeptide is a fusion protein. A further aspect of the invention is the use of the polypeptide as set forth above as an immunogen for the production of antibodies. Methods of production of the cleavage product, e.g. by recombinant means, are also provided.

In a specific embodiment, the invention relates to a recombinant cell producing one or more of the polypeptides of SEQ ID NO: 13, 14, 15, 16, 17, 18, 19, 20, 21, 22, 23, 24, 25, 26, 27, 28, 29, 30 and 31, preferably a recombinant form of the polypeptide. In another embodiment, the present invention relates to use of such a recombinant cell in a method for identifying compositions which modulate expression or activity of hemojuvelin.

In another aspect, the invention relates to a polynucleotide encoding an HFE2A polypeptide having an amino acid sequence with at least 60% identity to an amino acid sequence selected from the group consisting of SEQ ID NO: 13, 14, 15, 16, 17, 18, 19, 20, 21, 22, 23, 24, 25, 26, 27, 28, 29, 30 and 31, wherein said polypeptide has the same biological function of HFE2A or a fragment thereof. Although polypeptides with higher sequence homologies of, for example, 70%, 80%, 90%, 95% or 98% are also contemplated by this invention.

In another embodiment, the invention relates to a polynucleotide encoding a fragment of HFE2A polypeptide, which fragment comprises a contiguous stretch of at least 4, 10, 20, 50, 100 or 150 amino acids of SEQ ID NO: 10, 11 and 12. Preferably, the recited fragment has the ability to modulate, e.g. agonize or antagonize, an HFE2A. More preferably, the recited fragment has a molecular weight between about 7 kDa and 43 kDa.

Preferably, the polynucleotide as set forth above relates to the nucleic acid sequence for HFE2A, including the genomic sequence, mRNA or cDNA, polymorphic, allelic, isoforms and mutant forms thereof, and nucleic acid constructs of the gene, including vectors, plasmids and recombinant cells and transgenic organisms containing or corresponding to HFE2A (or knock-outs thereof).

In another embodiment, the present invention also relates to a recombinant cell comprising one or more of said polynucleotides encoding the HFE2A fragments of SEQ ID NO: 13, 14, 15, 16, 17, 18, 19, 20, 21, 22, 23, 24, 25, 26, 27, 28, 29, 30 and 31, including recombinant forms of the polynucleotides. Use of the recombinant cell to identify compositions that modulate expression or activity of HFE2A is part of this invention.

In another aspect, the present invention relates to a method for identifying an agent that modulates HFE2A, comprising contacting an HFE2A with a test compound and determining a change in HFE2A activity due to the compound, thereby identifying a modulator of HFE2A.

In a specific embodiment, a method for identifying an agent that modulates the activity of HFE2A comprising:

(a) contacting an HFE2A polypeptide with a test compound in the presence of a composition and under conditions conducive to cleavage of the HFE2A polypeptide by one or more component of the composition; and (b) detecting or measuring the presence or amount of HFE2A cleavage products that result from the cleavage, in which a difference in the presence or amount of said HFE2A cleavage products compared to the HFE2A polypeptide in presence of a composition not contacted with the test compound, thereby identifying a modulator of HFE2A activity.

The detection of the full-length HFE2A and of HFE2A cleavage products can be carried out by methods well known to those skilled in the art, e.g. precipitation or binding to an immobilized binding partner (plate or column) or using antibodies against the HFE2A or fragments thereof.

In yet another aspect of the present invention, HFE2A is incorporated into a screening assay whereby compounds (potential therapeutic agents) are tested to determine if they modulate HFE2A gene expression activity or protein expression levels, thereby identifying potential therapeutic agents.

The present invention further relates to a method for identifying an agent that modulates HFE2A gene expression, comprising contacting a polynucleotide comprising a HFE2A gene or fragments thereof with a test compound and under conditions promoting expression of said gene (i.e., conditions wherein the polynucleotide is being expressed) and determining a change in expression due to the presence of the test compound. Such methods identify the test compound as such a modulator of HFE2A.

In specific embodiments, the modulation is an increase or decrease in the expression level. Physiological benefits of an increase or decrease in the activity or expression of HFE2A include, but are not limited to, the treatment of Anemia of Chronic Disease or iron overload disorders such as hemochromatosis. Thus, the determination of the ability of agents to modulate such activity or expression affords an opportunity to discover useful therapeutic agents producing such effects.

In a specific embodiment, this change in expression is detected as a change in transcription of the HFE2A gene or the level or amount of the full-length protein or a cleavage fragment of the HFE2A, preferably where the gene is a mammalian gene and most preferably where the gene is expressed by a cell, preferably mammalian cells, especially human cells. In another embodiment, the expression level is determined by determining the level of mRNA produced after contact of said cell with said agent.

In one embodiment of such methods, the HFE2A-encoded polypeptide is a full length HFE2A. In another embodiment, the HFE2A-encoded polypeptide is a fragment of the full length HFE2A. In yet another embodiment, the HFE2A fragment comprises an amino acid sequence selected from SEQ ID NO: 13, 14, 15, 16, 17, 18, 19, 20, 21, 22, 23, 24, 25, 26, 27, 28, 29, 30 and 31.

In another embodiment, the gene whose modulation is to be determined is present in a mammalian cell, preferably a recombinant cell, including where the cell is a macrophage, inflammatory cell, liver cell, hepatocyte, intestinal cell, hematopoietic cell, pancreatic cell, skeletal muscle cell or a cell of the nervous system.

In another aspect, the present invention relates to a method for identifying an agent that modulates the level, amount or activity of an HFE2A polypeptide comprising:

a) contacting a test compound with an HFE2A polypeptide and under conditions supporting an activity of said polypeptide; and b) determining a change in said activity of said polypeptide as a result of said contacting, wherein a change in the activity identifies said test compound as an agent that modulates the level, amount or activity of an HFE2A polypeptide.

In one embodiment of such methods, the HFE2A-encoded polypeptide is a full length HFE2A. In another embodiment, the HFE2A-encoded polypeptide is a fragment of the full length HFE2A. In yet another embodiment, the HFE2A fragment comprises an amino acid sequence selected from the amino acid sequence of SEQ ID NO: 13, 14, 15, 16, 17, 18, 19, 20, 21, 22, 23, 24, 25, 26, 27, 28, 29, 30 and 31.

In other embodiments, the modulation is a decrease or increase in said biological activity. In a useful embodiment, the polypeptide is in, or is part of, a cell, preferably a mammalian cell, most preferably a recombinant cell, including where the cell is a macrophage, inflammatory cell, liver cell, hepatocyte, intestinal cell, hematopoietic cell, pancreatic cell, skeletal muscle cell or a cell of the nervous system. In other preferred embodiments, the cell has been engineered to produce said polypeptide, such as by genetic engineering, especially where said cell does not express said polypeptide absent said engineering.

In a specific embodiment of such methods, the agent is an anti-HFE2A polypeptide antibody, a peptide, a small molecule, a ribozyme, an antisense HFE2A nucleic acid molecule or the hemojuvelin polypeptide itself or fragments thereof. In one preferred embodiment, said agent is a fragment of the HFE2A polypeptide. It is contemplated that such fragments could serve directly as the therapeutic modulator of the hemojuvelin gene in order to treat iron overload, Anemia of Inflammation and other disorders of iron metabolism.

In a further aspect, the present invention relates to a method for identifying an agent that modulates the activity of an HFE2A polypeptide activity or fragments thereof, comprising;

(a) contacting a chemical agent with said HFE2A polypeptide under conditions promoting protein:protein interactions, and/or (b) contacting a chemical agent with said HFE2A polypeptide under conditions promoting HFE2A ligand HFE2A receptor interactions, and/or (c) contacting a chemical agent with said HFE2A polypeptide under conditions promoting modifications in lipid composition, and/or (d) contacting a chemical agent with said HFE2A polypeptide under conditions promoting alterations in associated second messenger signaling wherein such interaction, alteration or modification indicates modulation and thereby identifying the chemical agent as an agent that modulates HFE2A polypeptide activity or amount of specific fragments of HFE2.

In specific embodiments of said methods, the modulation may be an increase or decrease in the activity of the HFE2A polypeptide of fragments thereof.

In one embodiment, the modulators as set out above may be a drug-like small molecule, an antibody, an antisense nucleic acid, a ribozyme or any other compound which modulates the activity of the protein. In another embodiment, such a modulator may be a component of hemojuvelin itself, i.e. cleavage products or fragments of the hemojuvelin, that may modulate the activity of hemojuvelin. Furthermore, such fragments could serve directly as the therapeutic modulator of the hemojuvelin gene in order to treat iron overload, Anemia of Inflammation and other disorders of iron metabolism and may increase or decrease the activity of the HFE2A.

On the basis of the disclosure herein, those skilled in the art are able to develop the claimed screening assay based on known types of assays available. Known types of assays include cell based, cell extract, or cell free assays. Such assays are typically radioactivity or fluorescence based (i.e. fluorescence, resonance transfer or FRET). Alternatively, screening may employ multicellular organisms, including genetically modified organisms or naturally occurring genetic variants. Screening assays may be manual or low throughput assays, or they may be high throughput assays which are mechanically/robotically enhanced.

The present invention also encompasses embodiments where the agents identified by the methods of the invention, or useful in the methods of the invention, may be present in the form of a composition for treating a disease of iron metabolism comprising a therapeutically effective amount of a polypeptide of the invention, or a pharmaceutically active fragment thereof, in a pharmaceutically acceptable carrier. In accordance therewith, the present invention specifically contemplates a method for treating a disease of iron metabolism comprising administering to a patient in need thereof a therapeutically effective amount of such a composition. In an embodiment thereof, the disease is juvenile hemochromatosis.

In a further aspect, the compounds identified by the assays disclosed herein, and the methods of treating patients with such compounds, are applied to alternative or additional indications beyond diseases of iron metabolism, which are found to be treatable by modulating HFE2A activity.

In a further aspect, the present invention relates to compounds that modulate HFE2A that may now be identified by those skilled in the art. These compounds include antibodies, antisense compounds, gene therapy vectors and proteins, peptides including HFE2-derived peptides or polypeptides, and small molecule organic compounds. The invention also comprises the use of these compounds for treatment of diseases associated with aberrant HFE2A activity, but may also be used for conditions without distinct aberrations in HFE2A activity. In one embodiment, compounds of the invention are used for the treatment of disease of iron metabolism.

In another aspect, the present invention relates to a method for producing a product comprising identifying an agent according to the process of the invention wherein said product is the data collected with respect to said agent as a result of said process and wherein said data is sufficient to convey the chemical structure and/or properties of said agent.

In a further aspect, the present invention relates to a method for treating and/or preventing a disorder in an animal comprising administering to an animal afflicted therewith, or at risk of developing said disorder, a therapeutically effective amount of an HFE2A modulator. In a preferred embodiment, the HFE2A modulator exhibits modulating activity in a method of the invention, most preferably wherein said agent was first identified as an HFE2A modulator using said method and was not otherwise known to have such activity. In a preferred embodiment of such method, the HFE2A modulator is a selective HFE2A agonist, or a selective HFE2A antagonist, or a component of hemojuvelin itself, i.e. cleavage products or fragments of the hemojuvelin, that may modulate the activity of hemojuvelin, including pharmaceutically acceptable salts thereof, and/or any combinations of these, including where these are in a pharmaceutically acceptable carrier. In an embodiment, said disorder is a disease of iron metabolism, including an iron overload disorder and/or an iron deficiency disorder. Such disease of iron metabolism may also include one or more of Type I diabetes, Type II diabetes and insulin resistance.

In another such embodiment, the present invention relates to a method of diagnosing individuals afflicted with or at risk of developing a disease of iron metabolism comprising determining a mutation or polymorphism in the polynucleotide encoding a fragment of an HFE2A polypeptide in an individual, wherein a mutation or polymorphism of said fragment identifies said individual as being afflicted with or at risk of developing a disease of iron metabolism.

In another aspect, the present invention relates to a method to diagnose individuals afflicted with or at risk of developing a disease of iron metabolism comprising:

(a) detecting the level, amount or activity of a fragment or set of fragments of an HFE2A polypeptide obtained in a sample from an individual;

(b) determining a difference in the level, amount or activity from step (a) relative to the level, amount or activity of an identical fragment or set of fragments of said HFE2A polypeptide in an individual not so afflicted or at such risk (i.e., an otherwise healthy individual), wherein said difference identifies said individual as being afflicted with or at risk of developing a disease of iron metabolism.

In accordance with such methods, said determining step (b) further comprising:

contacting the sample of (a) with a binding agent; and detecting in the sample amount of said fragment that binds to the binding agent;

wherein the binding agent is a monoclonal or a polyclonal antibody.

In another aspect of such methods, said change is a decrease. In yet another aspect of such methods, said change is an increase.

In yet another such embodiment, the present invention relates to a method of diagnosing individuals afflicted with or at risk of developing a disease of iron metabolism comprising:

(a) obtaining a sample, such as a biological sample, from said individual and determining the level, amount or activity of a HFE2A polypeptide or fragments thereof and an iron metabolism protein; and (b) calculating a ratio of the level, amount or activity of the HFE2A polypeptide or the fragments relative to the iron metabolism protein; and (c) comparing the ratio to that in an individual not so afflicted with or at such risk;

wherein an altered ratio identifies said individual as being afflicted with or at risk of developing a disease of iron metabolism.

In accordance with such methods, the iron metabolism proteins may function as an internal standard for diagnosing diseases of iron metabolism and preferably selected from the group consisting of hepcidin, ferroportin, HFE, TFR1, TFR2, soluble transferrin receptor 1, haptoglobin and DMT1. It is understood by those skilled in the art that other proteins may also work as internal standards. In one embodiment, there is a direct relationship between the level, amount or activity of the full length HFE2A polypeptide or fragments thereof and the iron metabolism proteins. Preferably, wherein an altered ratio of the HFE2A or the fragments relative to the iron metabolism protein is predictive of individuals that are afflicted with or at risk of developing a disease of iron metabolism.

In one example, those skilled in the art may measure ratio of the level, amount or activity of the HFE2A polypeptide or the fragments relative to hepcidin. This may be useful to diagnose individuals that are afflicted with or at risk of developing anemia of inflammation when the results indicate an increase of the hepcidin relative to the HFE2A polypeptide or the fragments. More specifically, wherein the altered ratio is an the increase of the hepcidin to the HFE2A polypeptide or the fragments by at least 2, 4, 10, 20, 25, 50, 75, 100, 200, 500, 1000, 2000, 5000, 10000 folds or more. Stated in the alternative, the measure of hepcidin/the HFE2A polypeptide or the fragments is at least 2.

In an alternative measurement, the altered ratio is a decrease of the hepcidin to the HFE2A or the fragments by at least 2, 4, 10, 20, 25, 50, 75, 100, 200, 500, 1000, 2000, 5000, 10000 folds or more for individuals afflicted with or at risk of developing hemochromatosis.

In yet another such embodiment, the present invention relates to a method for differential diagnosis between an individual having anemia of chronic diseases and having iron deficiency anemia comprising:

(a) obtaining a sample, such as a biological sample, from an individual to be tested;

(b) detecting the level, amount or activity or relative ratio of a HFE2A polypeptide or fragments thereof in said sample; and (c) determining the difference in the level, amount or activity or relative ratio from step (b) relative to the level, amount or activity or relative ratio of said HFE2A polypeptide or said fragments thereof in an individual afflicted with either anemia of chronic diseases or iron deficiency anemia, wherein the level, amount or activity or relative ratio of HFE2A polypeptide or the fragments is different in each of these diseases;

thereby determining whether said individual has anemia of chronic diseases or has iron deficiency anemia.

In accordance with such methods, and in addition to above determination of the HFE2A polypeptide or the fragments, further comprising the step of measuring the level, amount or activity or relative ratio of at least one, but possibly more, other iron metabolism proteins selected from the group consisting of hepcidin, ferroportin, HFE, TFR1, TFR2, soluble transferrin receptor 1, haptoglobin and DMT1, thereby assisting in the accurate determination as to whether said human has anemia of chronic diseases or has iron deficiency anemia. The combined assessment of HFE2A and the activity or level of additional protein or proteins of iron metabolism allows for a more accurate diagnosis. Such an assessment could include but not limited to comparison of the ratio of HFE2A to protein or proteins of iron metabolism, or a composite pattern of expression of a panel of these proteins (or their corresponding genes) could be evaluated.

One may employ any method known to those skilled in the art to characterize the level, amount or activity of said iron metabolism protein, e.g. immunodiagnostic method by use of an antibody may be helpful. In accordance with such methods, the samples may include blood, plasma, serum, urine, saliva, cerebral spinal fluid, skin, liver and fractions thereof.

The present invention also contemplates a method for identifying a compound capable of modulating a HFE2A activity or level, comprising:

(a) contacting a cell which expresses HFE2A with a test compound; and (b) assaying the ability of the test compound to modulate the transcription of a HFE2A nucleic acid or the level or activity of HFE2A Polypeptide or an HFE2A fragment;

thereby identifying a compound capable of modulating level or activity of an HFE2A or HFE2A fragment.

In accordance with such methods, the compound is an anti-HFE2A polypeptide antibody, a ribozyme or is an antisense HFE2A nucleic acid molecule. In one preferred embodiment thereof, the compound is a HFE2A protein itself or a fragment thereof or a peptide derived from HFE2A. In another embodiment, the compound is a small organic molecule.

The present invention also encompasses embodiments where the agents identified by the methods of the invention, or useful in the methods of the invention, may be present in the form of a composition for treating a disease of iron metabolism comprising a therapeutically effective amount of a polypeptide of the invention, or a pharmaceutically active fragment thereof, in a pharmaceutically acceptable carrier. In accordance therewith, the present invention specifically contemplates a method for treating a disease of iron metabolism comprising administering to a patient in need thereof a therapeutically effective amount of such a composition. In preferred embodiments, the disease is Anemia of Chronic Disease or hemochromatosis. In another embodiment thereof, the disease is juvenile hemochromatosis.

In a further aspect, the present invention relates to a method for identifying an agent for the treatment of a disease of iron metabolism, comprising:

(a) administering to an animal an agent found to have activity using a method as disclosed herein, and (b) detecting in said animal a change which is indicative of a change in iron metabolism due to said administering, thereby identifying an agent for the treatment a disease of iron metabolism.

In a specific embodiment, the change in iron metabolism may be a change in storage or tissue distribution of iron or in the level of plasma iron and iron metabolism related parameters such as ferritin and transferrin saturation In another embodiment of the invention, the compound identified which modulates HFE2A is relatively selective for HFE2A ahead of related genes or proteins, and therefore may not significantly modulate the activity of such other related genes or proteins by direct interaction.

In another embodiment, the present invention relates to a method for selecting a therapeutic agent for use in an individual afflicted with or predisposed to developing a disease of iron metabolism comprising:

(a) administering to said individual a candidate agent and determining the HFE2A profile of a sample obtained from said individual; and (b) comparing said HFE2A profile with that of a person not so afflicted or predisposed, wherein if the HFE2A profile of step (b) is the same or similar to that of step (a) then said candidate agent is identified as a drug useful in treating said individual.

In a further aspect, the present invention is directed to a method for selecting a therapeutic agent for use in an individual afflicted with or predisposed to developing a disease of iron metabolism comprising:

(a) administering to said individual a candidate agent and determining the HFE2A profile of a sample obtained from said individual; and (b) comparing said HFE2A profile with that of a person known to be so afflicted or predisposed and which person is receiving a therapeutic agent known to ameliorate said affliction or predisposition, wherein if the HFE2A profile of step (b) is substantially the same as that of step (a) then said candidate agent is identified as a drug useful in treating said individual of step (a) and wherein if the HFE2A profile of step (b) is not substantially the same as that of step (a) then said candidate agent is identified as a drug not useful in treating said individual of step (a).

In another aspect, the present invention is related to a method for excluding a therapeutic agent for use in an individual afflicted with or predisposed to developing a disease of iron metabolism comprising:

(a) determining the HFE2A profile of a sample obtained from an individual receiving an agent believed to have therapeutic effect against hemochromatosis; and (b) comparing said HFE2A profile with that of a person not so afflicted or predisposed, wherein if the HFE2A profile of step (b) is substantially different from that of step (a) then said candidate agent is identified as not being useful in an individual so afflicted or predisposed.

Such "HFE2A profile" or "hemochromatosis profile" would be more or less defined as the relative ratio of level, amount or activity of one or two or more of any of HFE2A polypeptides and/or fragments thereof.

In preferred embodiments, the present invention is related to a method for selecting an appropriate therapeutic for an individual afflicted with or predisposed to developing a disease of iron metabolism comprising:

(a) detecting the level, amount or activity of an HFE2A polypeptide or fragments thereof from a sample obtained from the individual; and (b) comparing the relative level, amount or activity obtained in step (a) with the level, amount or activity of an HFE2A polypeptide or fragments previously obtained and associated with a known response to the therapeutics, wherein if the level, amount or activity obtained in step (a) is similar from the previously identified known response, the therapeutic would be selected for the individual.

In accordance with such methods, wherein the protein of iron metabolism is selected from the group consisting of hepcidin, ferroportin, HFE, HFE2A, TFR1, TFR2, soluble transferring reporter 1, haptoglobin and DMT1.

HFE2A Protein

FIG. 1 illustrates alternative splice variants that are generated during transcription of the HFE2A gene. For convenience, the nucleotide sequences of the coding exons are set out as follows in Table 1:

TABLE 1

| SEQ ID NO. | Description |
| --- | --- |
| 1 | Sequence of Exon 1 |
| 2 | Sequence of Exon 2 |
| 3 | Sequence of Exon 3a |
| 4 | Sequence of Exon 3b |
| 5 | Sequence of Exon 4 |

The alternative splice variants generated from the gene produce at least 5 transcripts. The nucleotide sequence of each of transcripts 1 to 4, corresponding to a cDNA sequence (or a processed mRNA sequence if T is converted to U) is set out as follows in Table 2:

TABLE 2

| SEQ ID NO. | Description |
| --- | --- |
| 6 | Wild-Type Human HFE2A putative cDNA - Transcript 1 (exon 1, 4) |
| 7 | Wild-Type Human HFE2A putative cDNA - Transcript 2 (exon 1, 3a, 4) |
| 8 | Wild-Type Human HFE2A putative cDNA - Transcript 3 (exon 1, 3b, 4) |
| 9 | Wild-Type Human HFE2A putative cDNA - Transcript 4 (exon 1, 2, 3b, 4) |

Each of these four transcripts of the HFE2A gene may be translated into an HFE2A polypeptide. Transcripts 1 and 2 generate the same proteins, hence there are 3 proteins of different sizes: 200 amino acids (a.a.), 313 a.a. and 426 a.a., respectively. The amino acid sequence generated from each transcript is set out as follows in Table 3:

TABLE 3

| SEQ ID NO | Description |
| --- | --- |
| 10 | Wild-Type Human HFE2A Polypeptide - Protein 1 (Transcripts 1 & 2) |
| 11 | Wild-Type Human HFE2A Polypeptide - Protein 2 (Transcript 3) |
| 12 | Wild-Type Human HFE2A Polypeptide - Protein 3 (Transcript 4) |

The longest cDNA sequence (Transcript 4, SEQ ID No. 9) and the longest protein sequence (Protein 3, SEQ ID No. 12) have been used as the basis for the sequencing numbering convention used in the instant specification.

Aspects of the sequence of HFE2A have been previously published in various sources, including the following: *Homo sapiens* Official Gene Symbol and Name: LOC148738; NCBI LocusID: 148738; Other Names: ENSG00000168509 (Ensembl v. 12.31.1), NM_145277 (RefSeq); Genomic Location: 142000393-142004657 bp on chromosome 1 (Assembly: NCBI 31 assembly of the human genome, Freeze Date: November 2002) (Ensembl Version for reference sequences: Ensembl v. 12.31.1.) A complete human HFE2A is contained in PCT publication WO 04/092405 and listed in GenBank as GB Ascension No. AY372521. The encoded amino acid sequence is available in GenBank under Ascension No. AAR22390 and is depicted as SEQ ID NO: 12.

HFE2A Cleavage Products

HFE2A is a critical regulator of iron metabolism. In particular, the present invention teaches that specific cleavage products of the HFE2A also play a key role in the regulation of iron metabolism. HFE2A cleavage products may modulate HFE2A activity through modulation of membrane bound HFE2A, thereby modulating hepcidin activity. Exactly how it is involved in this process remains to be fully clarified. Important information about the activity of these cleavage products can be determined based on the bioinformatics analysis of protein domains. It is possible to predict the putative cleavage sites and thus the identity of the specific cleavage products of HFE2A analyzing the known amino acid sequence. The longest protein sequence 426 aa LOC148738 (Protein 3, SEQ ID No. 12) was used for this analysis.

Figure 4A:
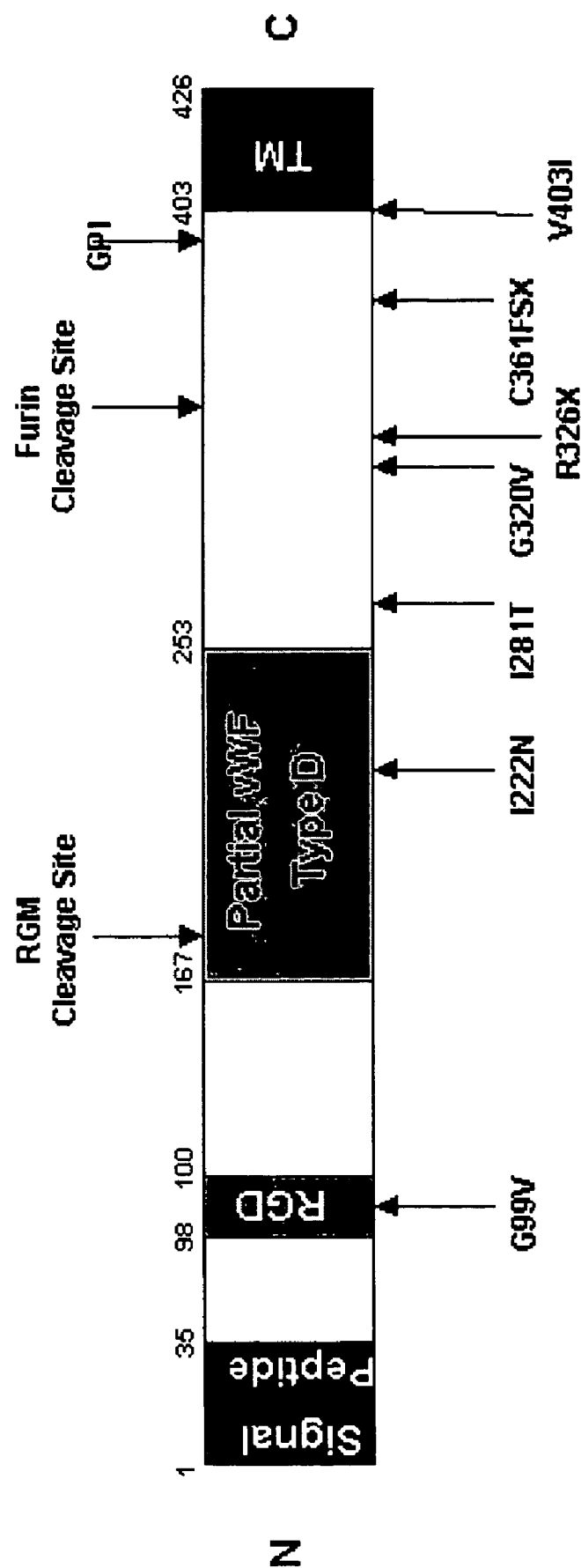
FIG. 4A—Structural features in the 426 aa translated open reading frame of HFE2A. RGD—cell attachment tri amino acid motif, vWF—Partial von Willebrand factor type D domain and TM—Transmembrane domain. Illustrated by arrows is the peptide cleavage site between positions S35 and Q36, a likely Asp/Pro proteolytic site between positions D172 and P173, a furin cleavage site between positions R335 and G336 and a predicted GPI modification site at position 400.
Figure 4B:
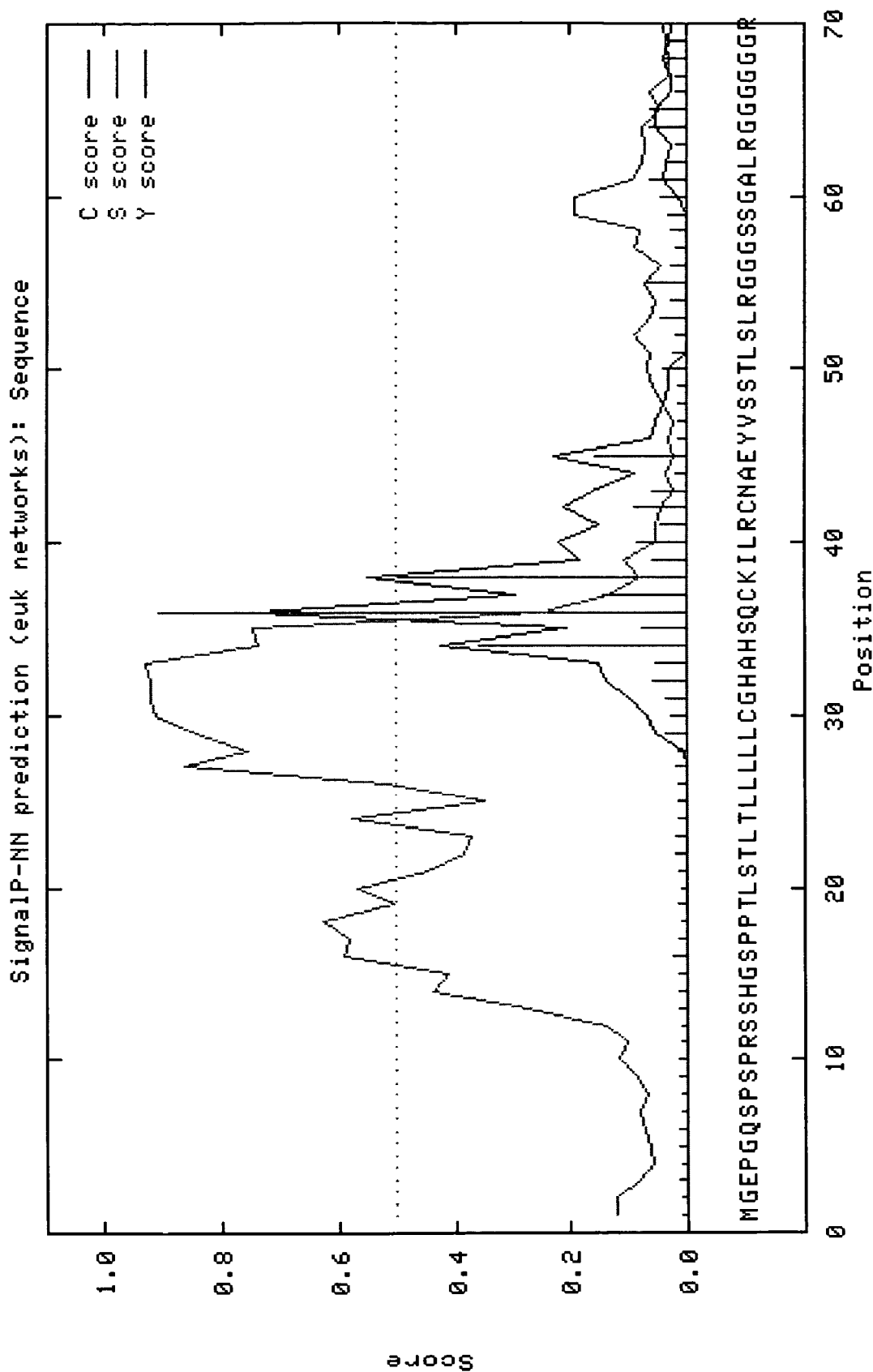
FIG. 4B shows the prediction of signal peptide cleavage site in 426 aa translation of HFE2A using SignalP (Henrik Nielsen et al. *Protein Engineering*, 10, 1-6 (1997)). Peptide cleavage site is predicted to be between S35 and Q36.
Figure 4C:
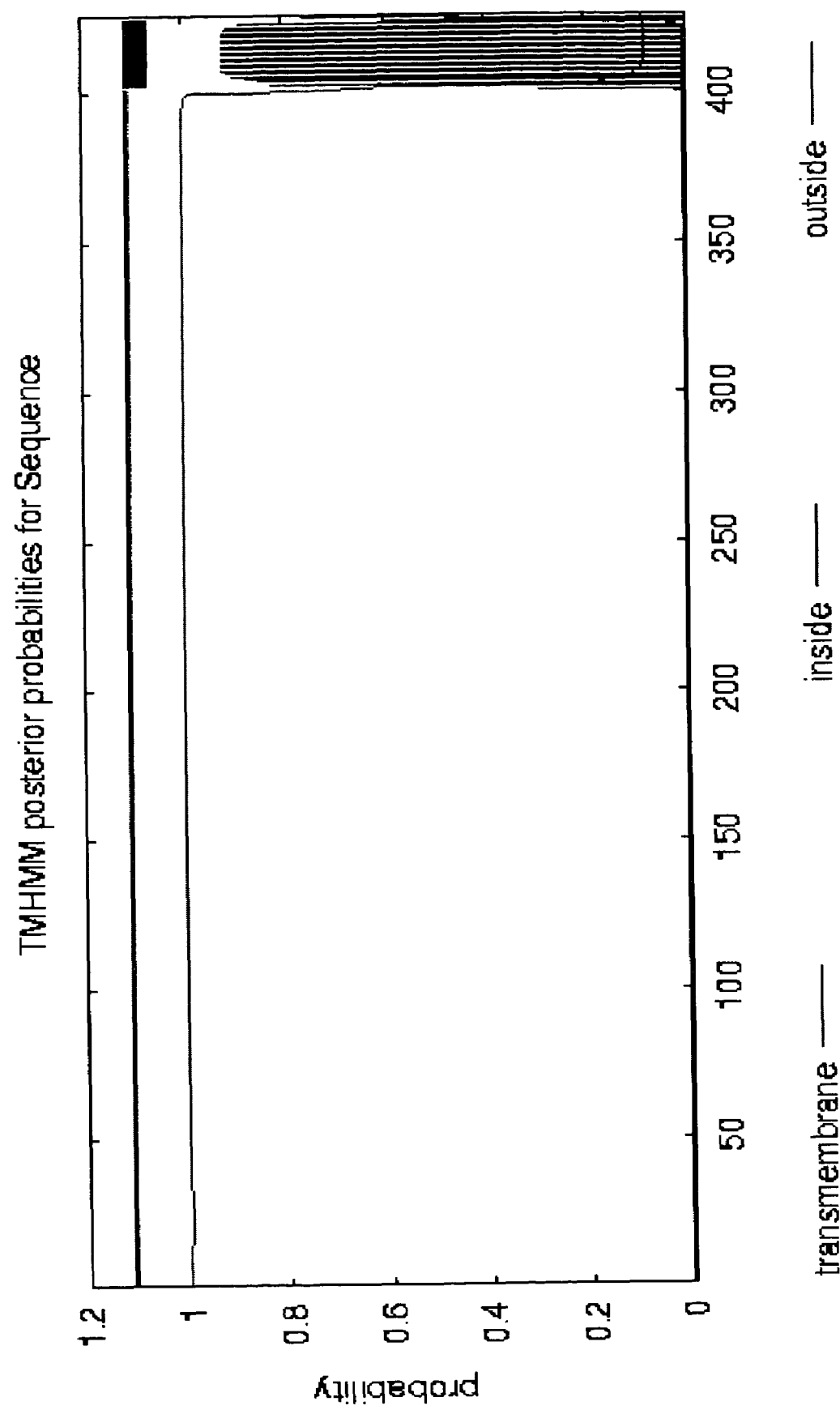
FIG. 4C shows the prediction of transmembrane regions in 426 aa translation of HFE2A using TMHMM. The transmembrane region is from residues 403-425.
Figure 4E:
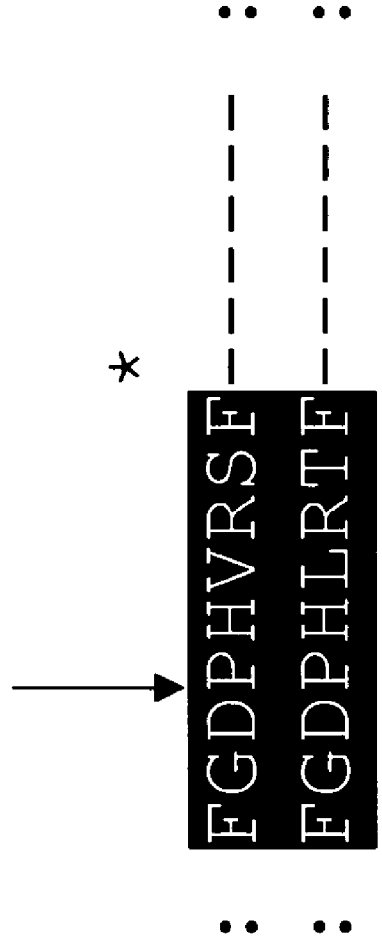
FIG. 4E shows proteolytic cleavage site (arrow) between residues 172D and 173P as identified by sequence comparison with Chicken Repulsive Guidance Molecule (RGM) (Monnier, et al., Nature, 419, 392-394, 2002).

The 426 aa LOC148738 gene product has structural features consistent with a GPI (Glycosylphosphatidylinositol) anchored protein (FIG. 4A) including a N terminal hydrophobic signal peptide for access to the Endoplasmic Reticulum, where GPI anchor addition occurs (residues 1-35 FIG. 4B) and a C terminal hydrophobic domain/GPI addition signal sequence (residues 403-425 FIG. 4C) (Udenfriend S and Kodukula K Ann Rev Biochem 1995). The GPI predicting program big-Pi predictor predicts that this gene product is GPI modified, and that either amino acids 399 or 400 can act as the omega site (Eisenhaber et al., JMB, 292 (3), 741-758, 1999). The LOC 148738 gene product has a predicted furin cleavage site representing the consensus cleavage site (Arg-X-Lys/Arg-Arg) for the proprotein convertase furin (Molloy et al., J. Biol. Chem., 267, 16396-16402, 1992) which would result in cleavage between residues 335 and 336 (FIG. 7F). In addition, the protein has a proteolytic cleavage site identified by sequence comparison with Chicken Repulsive Guidance Molecule (RGM) between residues 172 and 173 (FIG. 7e) (Monnier, P. P. et al. Nature 419, 392-394, 2002).

Accordingly, HFE2A may be GPI anchored to the cell membrane, or it may also exist in vivo in a soluble form that has been released from the GPI anchor or additional cleavage sites may be utilized thereby releasing smaller HFE2A polypeptides. For non-limiting example, cleavage using the furin cleavage site could potentially result in a significant portion of the protein being released from the cell membrane. In another non-limiting example, the HFE2A is cleaved via the GPI anchor between amino acid 400 and 401 to generate the soluble fragment. Another possibility is that a non-specific or specific proteolytic cleavage of the receptor ectodomain could also generate a soluble HFE2A fragment. In one embodiment, one specific cleavage product can be released from the HFE2A, while in other embodiments, two or more specific cleavage products can be released from the cleavage. There are numerous precedents for soluble forms of membrane bound receptors including for example growth hormones and leptin as well as many cytokines.

By way of non-limiting examples, the possible cleavage sites within the amino acid sequence of HFE2A include: the N-terminal signal peptide between amino acids 35 and 36, the Asp/Pro autocatalytic cleavage between amino acids 172 and 173, the furin cleavage between amino acids 335 and 336, and the GPI anchor cleavage between amino acids 400 and 401.

Figure 5:
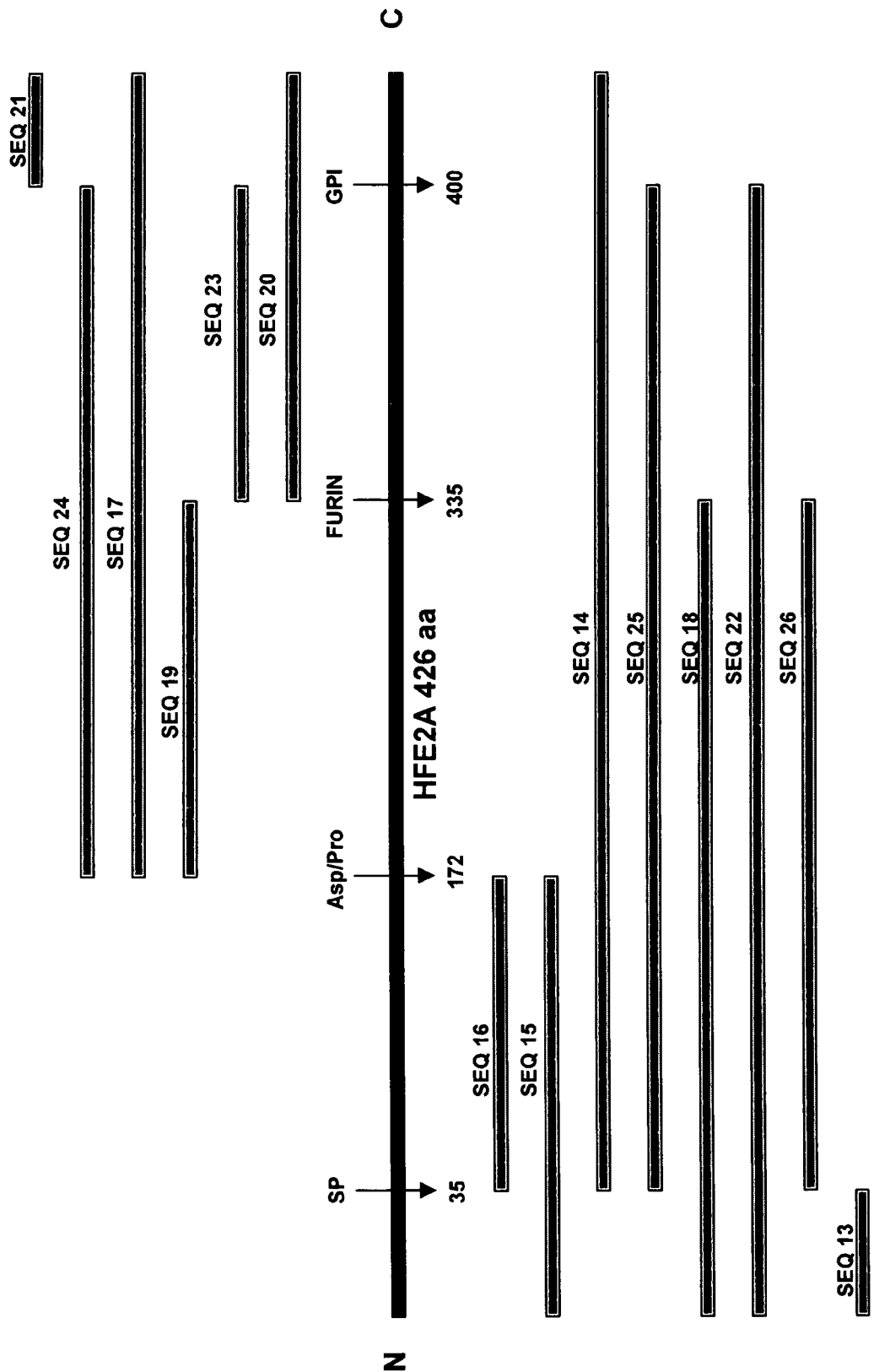
FIG. 5 shows a schematic diagram of the 426 aa translated open reading frame for HFE2A illustrating the positions of the predicted cleavage products for SEQ ID NO: 13-26 identified by sequence analysis. Arrows indicate potential cleavage sites.

FIG. 4 shows a protein domain analysis of HFE2A from a nucleotide/amino acid perspective. Features of the sequence are illustrated therein. From this we predict the generation of the following fragments for the 426 aa gene product (Protein 3/SEQ ID NO: 12) (FIG. 5)

TABLE 4

| SEQ ID NO | From aa | To aa | Size | Cleavage Product |
|---|---|---|---|---|
| 13 | 1 | 35 | 3.6 kDa | N-terminal signal peptide |
| 14 | 36 | 426 | 41.5 kDa | C-terminal signal peptide |
| 15 | 1 | 172 | 17.6 kDa | N-terminal Asp/Pro peptide |
| 16 | 36 | 172 | 14.0 kDa | N-terminal Asp/Pro peptide (minus N-terminal signal peptide) |
| 17 | 173 | 426 | 27.5 kDa | C-terminal Asp/Pro peptide |
| 18 | 1 | 335 | 35.3 kDa | N-terminal Furin peptide |
| 19 | 173 | 335 | 17.8 kDa | Asp/Pro to Furin peptide |
| 20 | 336 | 426 | 9.8 kDa | C-terminal Furin peptide |
| 21 | 401 | 426 | 2.7 kDa | C-terminal Furin GPI peptide |
| 22 | 1 | 400 | 42.4 kDa | N-terminal GPI anchor peptide |
| 23 | 336 | 400 | 7.1 kDa | Furin to GPI anchor peptide |
| 24 | 173 | 400 | 24.9 kDa | Asp/Pro to GPI anchor peptide |
| 25 | 36 | 400 | 38.9 kDa | Signal to GPI anchor peptide |
| 26 | 36 | 335 | 31.7 kDa | Signal to Furin peptide |

For the 200 aa gene product (Protein1/SEQ ID NO: 10), we predict the generation of the following fragments:

TABLE 5

| SEQ ID NO | From aa | To aa | Size | Cleavage Product |
|---|---|---|---|---|
| 27 | 1 | 109 | 11.7 kDa | N-terminal Furin peptide |
| 28 | 1 | 174 | 18.8 kDa | N-terminal GPI anchor peptide |

For the 313 aa gene product (Protein2/SEQ ID NO: 11), we predict the generation of the following fragments:

TABLE 6

| SEQ ID NO | From aa | To aa | Size | Cleavage Product |
|---|---|---|---|---|
| 29 | 1 | 59 | 6.2 kDa | N-terminal Asp/Pro peptide |
| 30 | 1 | 222 | 23.9 kDa | N-terminal Furin peptide |
| 31 | 1 | 287 | 31.0 kDa | N-terminal GPI anchor peptide |

Other features identified are a RGD—cell attachment tri amino acid motif (residues 98-100) (Ruoslahti, E. Annu. Rev. Cell Dev. Biol. 12, 697-715 (1996)) and a partial von Willebrand factor type D domain. von Willebrand factor type D domains are required for multimerization of von Willebrand factor (residues 167-253) (Jorieux, S. et al., Blood 1998 Dec. 15; 92(12):4663-70). Also present but not shown are N-glycosylation and O-glycosylation sites which appear to be consistent with consensus sequences.

The HFE2A cleavage product of the invention can be produced by various methods known in the art. The manipulations which result in their production can occur at the gene or protein level.

Furthermore, the genetic construct may be incorporated into a cell, preferably a mammalian cell, such as where the mammalian cell is a macrophage, liver cell, hepatocyte, intestinal cell, inflammatory cell, liver cell, hepatocyte, intestinal cell, hematopoietic cell, pancreatic cell, skeletal muscle cell or a nervous system cell.

Manipulations of the HFE2A cleavage product may also be made at the protein level. For example, a specific cleavage product can be released by treatment of the full length protein with one or more cleavage agents. This treatment can be accomplished via an in vitro cleavage reaction in which one or more cleavage agents are added to a HFE2A containing sample. The cleavage agents cleave peptide bonds between particular amino acids in a polypeptide and thereby release the specific cleavage products. Examples of proteolytic cleavage agents are enzymes such as furin, but would also include other proteases not yet know to cleave HFE2A, such as for example pepsin, thrombin, trypsin.

Included within the scope of the invention are HFE2A cleavage product which are differentially modified during or after translation, e.g., by glycosylation, acetylation, phosphorylation, amidation, derivatization by known blocking/protecting groups, linkage to an antibody molecule or other cellular ligand, etc. In addition, analogs and derivatives of the HFE2A cleavage products can be chemically synthesized by methods known in the art, e.g., by use of peptide synthesizer.

In vitro assay to determine the effect of modulators of HFE2A level and/or activity include assays that detect protein amounts as well as assays that detect functional activity of the HFE2A protein. Assay that detect protein amounts and sizes include various combinations of western blotting, immunodot blotting and elisa assays. Assay that determine HFE2A activity comprise using a cell line recombinant which expresses HFE2A. The readout of the HFE2A activity is the expression (mRNA or protein) of hepcidin. The assay comprises contacting the cell with the test modulator (compound or HFE2A fragment itself), and measuring the impact on hepcidin expression.

Table 7 below sets forth polymorphisms that have been identified in the HFE2A gene of control individuals (i.e. those with no clinical manifestation of Juvenile Hemochromatosis or other iron metabolism disorder). These polymorphisms, and others that may be discovered by those skilled in the art, may be useful for diagnostic or therapeutic or other purposes.

TABLE 7

| Mutation | Type | Sequence |
|---|---|---|
| c.1-15C > G, na | WT | gcctgggaaaCctggctggat (SEQ ID NO: 32) |
| | MT | gcctgggaaaGctggctggat (SEQ ID NO: 33) |
| c.98-6C > G, intronic 2-3 | WT | tcccttctgtCtttagctcat (SEQ ID NO: 34) |
| | MT | tcccttctgtGtttagctcat (SEQ ID NO: 35) |
| c.205_206insAGG, p.G69_70insG | WT | gaggaggagg---ccggggtgga (SEQ ID NO: 36) |
| | MT | gaggaggaggAGGccggggtgga (SEQ ID NO: 37) |
| c.432C > G, p.A144A | WT | gcctccctgcCccggaccctt (SEQ ID NO: 38) |
| | MT | gcctccctgcGccggaccctt (SEQ ID NO: 39) |
| c.483C > A, p.P161P | WT | atggtcgtccCccggggttct (SEQ ID NO: 40) |
| | MT | atggtcgtccAccggggttct (SEQ ID NO: 41) |
| c.488G > C, p.G163A | WT | cgtcccccggGgttcttgcat (SEQ ID NO: 42) |
| | MT | cgtcccccggCgttcttgcat (SEQ ID NO: 43) |
| c.569C > A, p.A190D | WT | gtccaaggagCttggcctcta (SEQ ID NO: 44) |
| | MT | gtccaaggagAttggcctcta (SEQ ID NO: 45) |
| c.627G > T, p.A209A | WT | cccccatggcGttggggggcca (SEQ ID NO: 46) |
| | MT | cccccatggcTttggggggcca (SEQ ID NO: 47) |
| c.682C > A, p.Q228K | WT | taagaacatgCaggaatgcat (SEQ ID NO: 48) |
| | MT | taagaacatgAaggaatgcat (SEQ ID NO: 49) |
| c.929C > G, p.A310G | WT | gccttctcagCtgaacaggac (SEQ ID NO: 50) |
| | MT | gccttctcagGtgaacaggac (SEQ ID NO: 51) |
| c.1207G > A, p.V403I | WT | agatgctgggGttcctctttc (SEQ ID NO: 52) |
| | MT | agatgctgggAttcctctttc (SEQ ID NO: 53) |

Capital letter indicates site and nature of polymorphism.
WT = wild-type;
MT = mutation.

Further aspects of HFE2A cleavage product function at the biochemical level may be determined by those skilled in the art using standard techniques. It is clear from the instant invention that HFE2A and cleavage products thereof are directly involved in iron transport, as the absence of this gene in humans leads to the condition of juvenile hemochromatosis (type 2A) or HFE2A. However, HFE2A and fragments thereof are highly expressed in muscle during early embryonic development and may play additional roles unrelated to iron metabolism. For example, HFE2A may serve as a marker for early myogenesis. This may have importance in stem cell identification for early muscle progenitors.

Sixteen human tissues were examined for HFE2A expression by probing Northern blots with a probe from exon 4. Significant HFE2A expression was detected in liver, heart (especially atria) and skeletal muscle (data not shown).

Based on publicly available ESTs (expressed sequence tags), fragments of this gene has also been found to be expressed in the following tissues:

Human HFE2A: skeletal muscle, liver, sciatic nerve, liver and spleen, prostate, heart;

Mouse HFE2A: mammary gland, heart, tongue, liver, xiphoid cartilage, medulla oblongata Rat HFE2A: brain, ovary, placenta, kidney, lung, liver, heart, muscle, spleen Therefore the HFE2A gene appears to be widely expressed in many tissues, but at reasonably low levels.

While not wishing to be bound to any particular mechanism of action of HFE2A cleavage products, it is possible to speculate on different roles the cleavage product of the invention may play in iron metabolism.

The cleavage product may serve to compete with the membrane bound form of HFE2A thereby modulating the activity of the membrane bound form of HFE2A. Such competition could occur for a critical activating ligand which is essential to membrance bound-HFE2A function. By competing out the ligand, HFE2A fragments modulate the activity of the full-length protein.

In another embodiment, HFE2A fragments may play as yet to be determined role as peptide/polypeptide hormonal messenger.

In another embodiment, HFE2A fragments may play as yet to be determined role as peptide/polypeptide autocrine or paracrine modulator.

For instance, the HFE2A protein may lie upstream or downstream of hepcidin in the iron metabolism pathway. In a prefered embodiment, HFE2A is upstream of hepcidin and modulates hepcidin activity.

One possibility is that HFE2A functions in the transcription, translation and/or processing of hepcidin, and is necessary for proper functioning of hepcidin. HFE2A may be a hepcidin interacting protein. HFE2A may be necessary for the mandatory processing of pro-hepcidin to its active form, hepcidin. An alternate function is that the HFE2A protein or portion thereof (ie a cleavage product), may be a secreted factor from the liver or muscle, acting in a paracrine or endocrine fashion, as a hormone or hormone-like compound which regulates hepcidin levels.

These possible mechanisms of action are suggestive for further exploration of function of the protein and cleavage products, but are not intended to be limiting on the scope of claims included below. In all of these scenarios, the functional consequences are the same, i.e. loss of function of HFE2A results in loss of the body's capacity to control iron metabolism through normal hepcidin function, thus precipitating the development of juvenile hemochromatosis, or adult onset hemochromatosis (possibly where other factors in the hepcidin/HFE2A metabolic pathway are not fully functional).

Thus, modulating the activity of HFE2A is a method to regulate serum levels, biodistribution, and/or metabolism of iron in the body.

Modulation of HFE2A is also a method for treating diseases which are not directly related to iron or iron metabolism. A function for HFE2A unrelated to its proposed role in iron metabolism is that of regulating blood volume. HFE2A is highly expressed in heart, especially in the right atrium, and therefore it is possible that HFE2A plays a biological role, such as in sensing circulating blood volume and the regulation of blood volume. Alternatively, HFE2A may play a paracrine function in the heart protecting local myocytes from iron related disease. Compounds which modulate the activity of HFE2A are therefore useful in treating or preventing cardiac disorders (including but not limited to cardiac failure, cardiomyopathy, disorders of fluid imbalance, and arrhythmias), and hormonal disorders. Also important, because hepcidin levels are stimulated in bacterial infections, inflammation, response to LPS injection, etc, HFE2A is a suitable therapeutic target for mediating aspects of these disorders, and could be important in treatment of bacterial sepsis, etc.

This invention establishes that the function of HFE2A is an essential regulator of iron in the human body, regardless of its exact mechanism of action. It is therefore a desirable drug target for treating diseases of iron metabolism in animals. For example, because HFE2A is directly implicated in JH and adult onset hemochromatosis according to this invention, the inventors recognize that JH and other diseases where iron metabolism is defective, may be treatable by administering a chemical or protein or peptide modulator of HFE2A. The disease may not necessarily be related to aberrant HFE2A gene or protein activity. For example, a compound which modulates HFE2A activity may compensate for insufficiencies in other aspects of the iron metabolism pathway. Or, a modulator of HFE2A may be used to treat a disease which is indirectly responding to iron levels in the blood.

As used in this disclosure the phrase "disease of iron metabolism" is therefore to be construed in its broadest context. This includes diseases where aberrant iron metabolism directly causes the disease, or where iron blood levels are disregulated causing disease, or where iron disregulation is a consequence of another disease, or where diseases can be treated by modulating iron levels, etc. More specifically, a disease of iron metabolism according to this disclosure includes iron overload disorders, iron deficiency disorders, disorders of iron biodistribution, other disorders of iron metabolism and other disorders potentially related to iron metabolism, etc. Even more specifically diseases of iron metabolism includes hemochromatosis, ferroportin mutation hemochromatosis, transferrin receptor 2 mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, african iron overload, hyperferritinemia, ceruloplasmin deficiency, atransferrinemia, congenital dyserythropoietic anemia, anemia of chronic disease, anemia, hypochromic microcytic anemia, iron-deficiency anemia, conditions with hepcidin excess, Friedriek's Ataxia, gracile syndrome, Hallervan Spatz disease, Wilson's disease, pulmonary hemosiderosis. In addition the phrase "disease of iron metabolism" also includes disorders not primarily due to defect in iron metabolism, but conditions that are exacerbated or modulated by iron metabolism disturbances such as hepatocellular carcinoma, cancer, hepatitis, cirrhosis of liver, pica, chronic renal failure, insulin resistance, diabetes, atherosclerosis, neurodegenerative disorders, Crohn's disease, multiple sclerosis, Parkinson's Disease, Huntington's Disease, Alzheimer's Disease.

In particular, a modulator of HFE2A can usefully treat anemia of chronic disease. Worldwide, anemia of chronic disease (ACD, also know as Inflammatory Anemia (AI)) is the second most common form of anemia. ACD represents the most common form of anemia in hospitalized patients. ACD is an acquired disorder seen in patients with a variety of conditions including infection, malignancy and chronic inflammation. It is characterized by retention of iron by macrophages and decreased intestinal iron absorption, which leads to reduced iron availability for erythropoiesis. Early in the course of their disease, patients with ACD have a mild, normocytic anemia due to impaired iron recycling. Later, due to the reduced intestinal absorption they become frankly iron deficient with a hypochromic microcytic picture. Initial studies examining the role of hepcidin in ACD show that excessive hepcidin production underlies ACD.

Loss-of-function of murine hepcidin leads to severe iron overload, mimicking the biochemical and clinical phenotype of JH. In contrast, in both animal models and human disease, hepcidin overexpression leads to macrophage iron retention and an iron deficient phenotype typical of the iron disturbances found in ACD. Existing therapy for ACD is mainly targeted to treating the underlying disorder, with no efficacious treatment specifically directed to amelioration of the iron phenotype. Therefore, therapeutic strategies to reduce hepcidin production, such as by inhibition of HFE2A or the modulation of HFE2A protein or expression represent an important novel approach to treating the iron disturbances seen in ACD.

In some cases the diseases and disorders included in the definition of "disease of iron metabolism" are not typically identified as being iron related. It is recognized by the instant invention that based on the tissue distribution of HFE2A (hemojuvelin) and its related protein, hepcidin, that iron metabolism may play a significant role in these disease processes. For example, it has recently been shown that hepcidin is very highly expressed in the murine pancreas suggesting that diabetes (Type I or Type II), insulin resistance, glucose intolerance and other disorders may be ameliorated or at least attenuated by treating underlying iron metabolism disorders: (See Ilyin, G. et al. 2003 Febs. Letters 542 22-26). As such, these diseases are encompassed under the broad definition.

Method of Treatment Using HFE2A Fragments as a Therapeutic Target.

The discovery that specific fragments of HFE2A have a role in regulating clearly definable physiological outcomes in humans (namely juvenile hemochromatosis), now allows the inventors to establish, for the first time, that HFE2A cleavage products are useful as therapeutic targets or as therapeutic agents themselves in humans for the treatment of diseases of iron metabolism. The words "therapeutic target" are intended to mean that therapeutic intervention is achieved with therapeutic agents that modulate the activity of the gene or protein. "Modulate" means to increase, to decrease, or to otherwise change the activity. Standard industrial processes are available to those skilled in the art to confirm the identity of the therapeutic agents which modulate the activity of the gene or protein, some of which are set out below.

In accordance with the foregoing, the present invention relates to a method for treating a disorder comprising administering to a person in need of such treatment an effective amount of a selective HFE2A agonist or antagonist, or a component of HFE2A itself, i.e. cleavage products or fragments of the HFE2A, that may modulate the activity of hemojuvelin, including a pharmaceutically acceptable salt thereof, or a pharmaceutical composition containing either entity.

In one embodiment, said disorder is a disease of iron metabolism. In a further embodiment, said administering includes but is not limited to intradermal, intramuscular, intraperitoneal, intravenous, subcutaneous, intranasal, epidural, and oral routes. Administration can be systemic or local. The amount of the therapeutic agent of the invention effective in the treatment of a particular disorder or condition depends on the nature of the disorder or condition and can be determined by standard clinical techniques. The precise dose to be employed in the formulation will also depend on the route of administration and the seriousness of the disease or disorder.

Use of the HFE2A in Screening Assays for Identifying Therapeutic Agents and Classes of Potential Therapeutic Agents.

The present invention readily affords different means for identification of agents for treating diseases of iron metabolism according to their ability to modulate the level, amount or activity of HFE2A. Exemplary assay methods useful for the identification of such compounds are detailed herein, although those skilled in the art will be aware of alternative means.

In one series of embodiments described in some detail below, assay methods involve testing libraries of chemical compounds, either one at a time or in combinations, in an assay format designed to measure a biological activity related to HFE2A. Those library compounds that modulate the biological activity in the desired fashion are thereby identified as therapeutic agents of the invention. In effect, a wide variety of compounds are sequentially tested against the assay to determine whether they influence a measurable biological activity of the assay. Assays may be based one or more of the diverse measurable biological activities of a gene or polypeptide corresponding to HFE2A or may include the measurement and detection of quantitative changes of different cleaved fragments of an HFE2A.

"HFE2A activity" or "HFE2A biological activity" as used herein, especially relating to screening assays, is to be interpreted broadly and contemplates all directly or indirectly measurable and identifiable biological activities of the HFE2A gene, gene products, HFE2A Polypeptide and fragments (i.e. cleavage products) thereof. Relating to the purified HFE2A Polypeptide protein, HFE2A Polypeptide activity includes, but is not limited to, all those biological processes, interactions, binding behavior, binding-activity relationships, pKa, pD, enzyme kinetics, stability, and functional assessments of the protein. Relating to HFE2A Polypeptide activity in cell fractions, reconstituted cell fractions or whole cells, these activities include, but are not limited the rate at which HFE2A Polypeptide performs any measurable biological characteristic and all measurable consequences of these effects, including cell growth, development or behavior and other direct or indirect effects of HFE2A Polypeptide activity. Relating to HFE2A genes and transcription, HFE2A activity includes the rate, scale or scope of transcription of genomic DNA to generate RNA; the effect of regulatory proteins on such transcription, the effect of modulators of such regulatory proteins on such transcription; plus the stability and behavior of mRNA transcripts, post-transcription processing, mRNA amounts and turnover, all measurements of expression and translation of the mRNA into polypeptide sequences, and all measurements of protein expression levels or dynamics. Relating to HFE2A activity in organisms, this includes but is not limited biological activities which are identified by their absence or deficiency in disease processes or disorders caused by aberrant HFE2A biological activity in those organisms. Some of the known or suggested biological activities are set out in the description of HFE2A provided in the specification, however those skilled in the art will be able to identify further measurable activities of HFE2A with routine techniques. Broadly speaking, HFE2A biological activity can be determined by all these and other means for analyzing biological properties of proteins and genes that are known in the art.

It is also recognized that those skilled in the art may prefer to use forms of HFE2A corresponding to the sequences disclosed herein, although not necessarily the same. For example, while screening assays preferably employ HFE2A from human, mouse, rat or fugu, other assays may utilize HFE2A from a different organism, preferably a vertebrate, and most preferably from a mammalian species. Thus the invention encompasses the use of, including but not limited to, sheep, dog, cow or horse HFE2A, in whole or part thereof, for the same purposes as set out more specifically herein for human HFE2A. The shared technical features of these forms of HFE2A, are that, when expressed, they have similar biological activity, and that they share functional similarity with HFE2A, as the case may be, such as may be determined by those skilled in the art. The HFE2A gene and/or HFE2A Polypeptide according to the invention may also be obtained from other mammalian species, other vertebrates, invertebrates and microorganisms based on the disclosure herein.

Thus, the polynucleotides for use in the screening assays of the invention that "correspond to" the polynucleotide encoding HFE2A (processed or unprocessed, including naturally occurring splice variants and alleles) are at least 60%, preferably at least 70%, more preferably at least 80%, especially at least 90%, even more preferably at least 95%, or even at least 98%, with the especially preferred embodiment of identical to, and especially having the sequence of, an RNA that would be encoded by, or be complementary to, such as by hybridization under reasonably stringent conditions, with an HFE2A polynucleotide (SEQ ID NO: 1-9.) or a polynucleotide encoding an HFE2A cleavage product (SEQ ID NO: 13-31). Thus, any such sequences are available for use in carrying out any of the methods disclosed according to the invention. Such sequences also include any open reading frames in whole or part thereof, as defined herein, present within an HFE2A polynucleotide.

Because of the processing that may take place in transforming the initial RNA transcript into the final mRNA, the sequences disclosed herein may represent less than the full genomic sequence. They may also represent sequences derived from alternate splicing of exons. Consequently, the genes present in the cell (and representing the genomic sequences) and the sequences disclosed herein, which are mostly cDNA sequences, may be identical or may be such that the cDNAs contain less than the full complement of exons found in the genomic sequence. Such genes and cDNA sequences are still considered corresponding sequences because they both encode similar RNA sequences. Thus, by way of non-limiting example only, a gene that encodes an RNA transcript, which is then processed into a shorter mRNA, is deemed to encode both such RNAs and therefore encodes an RNA corresponding to an HFE2A sequence as disclosed herein. (Those skilled in the art understand that the word "encode" and its derivatives mean, in this field "can be transcribed into" or "can be translated into"). Thus, the sequences disclosed herein correspond to genes contained in the cells and are used to determine relative levels of transcription because they represent the same sequences or are complementary to RNAs encoded by these genes. Such genes also include different alleles and splice variants that may occur in the cells used in the processes of the invention.

As used herein, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100 [1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

Where context indicates that sequences have been analyzed using the NCBI Blast tools, reports of sequence score, alignment, identity %, postive % and gaps % have been generated based on these calculations: For the segment pair, the alignment score is the sum of the scoring matrix values. The theory of amino acid substitution matrices is described in [1], and applied to DNA sequence comparison in [2]. The number of positives is the number of residues for which the alignment score has a positive value. Experimentation has shown that the BLOSUM-62 matrix [3] is among the best for detecting most weak protein similarities. [1] Altschul, S. F. (1991) "Amino acid substitution matrices from an information theoretic perspective." J. Mol. Biol. 219:555-565. [2] States, D. J., Gish, W. & Altschul, S. F. (1991) "Improved sensitivity of nucleic acid database searches using application-specific scoring matrices." Methods 3:66-70. [3] Henikoff, S. & Henikoff, J. G. (1992) "Amino acid substitution matrices from protein blocks." Proc. Natl. Acad. Sci. USA 89:10915-10919.

As used herein, the terms "portion," "segment," and "fragment," when used in relation to polypeptides, refer to a continuous sequence of nucleotide residues, sequence forms a subset of a larger sequence. Such terms include the products produced by treatment of said polynucleotides with any of the common endonucleases, or any stretch of polynucleotides that could be synthetically synthesized. These may include exonic and intronic sequences of the corresponding genes. For predicted expression products see Tables 4-6 above.

The instant invention provides numerous assays which measure an activity of HFE2A or protein levels or levels of HFE2A protein framents and are useful for the testing of compounds to identify which ones affect such activity. In terms of formatting the assays, the assays may use whole cells, cell extracts or reconstituted cell extracts, or purified or semi-purified proteins, or they may be larger scale tissue or whole animal assays. Common assays use measurements based on fluorescence, luminescence, radioactivity, or other measures of protein or gene transcript levels, amounts, or stability. Polypeptide assays may also include those wherein the HFE2A polypeptide is attached to a solid support, such as a resin or other polymer, especially where this is part of a column procedure for determining activity. Alternatively, batch procedures may also be used.

In one aspect, the present invention relates to a method for identifying an agent that modulates the activity of an HFE2A polypeptide or the amount of the polypeptide or the amount of HFE2A protein fragments, comprising:

a) contacting a test compound with an HFE2A polypeptide and under conditions supporting an activity of said polypeptide; and b) determining a change in said activity of said HFE2A polypeptide or the amount of the polypeptide or the amount of HFE2A protein fragments as a result of said contacting, wherein a change in the activity or amount identifies said test compound as an agent that modulates the activity or amount of an HFE2A polypeptide.

In a preferred embodiment, said polypeptide has the sequence of SEQ ID NO: 13-31.

In a preferred embodiment, the observed change in activity in step (b) is a decrease or an increase in activity or amount, most preferably wherein said change in activity is the result of binding to said polypeptide by said compound of step (b). In a preferred embodiment, such agents are useful for treating a disease of iron metabolism.

In other preferred embodiments, the polypeptide is part of an intact cell, preferably a mammalian cell, and which may be a recombinant cell. For HFE2A, cells of greatest interest include macrophages, hepatocytes, intestinal cells, heart cells (especially atrial cells), pancreatic cell, skeletal muscle cell and cells of the bone marrow, although cells from other tissues may be employed. In one such embodiment, said cell has been engineered to comprise said polypeptide or fragment thereof, including by genetic engineering, especially where the cell does not possess the polypeptide absent said engineering, but may possess such said polypeptide. Thus, the present invention specifically contemplates embodiments in which the cell is engineered by other than genetic engineering such as where the activity of a polypeptide is to be enhanced and the cell has been engineered to contain, or have on its surface, said polypeptide but wherein the polypeptide is present due to physical insertion of the polypeptide into the membrane or cytoplasm of the cell and not through endogenous expression of a gene contained in the cell Methods well known in the art, such as use of polyethylene glycol, viruses, and the like, are available to effect such insertions and the details of such procedures need not be further described herein.

In one preferred embodiment of such method, the polypeptide is a polypeptide that reacts with an antibody that reacts with, or is specific for, a polypeptide having an amino acid sequence at least 95% identical to, more preferably at least 98% identical to, the sequence of SEQ ID NO: 13-31 and where any difference in amino acid sequence is due only to conservative amino acid substitutions. In an especially preferred embodiment, the polypeptide has the amino acid sequence of SEQ ID NO: 13-31.

The HFE2A Polypeptide assays of the invention may employ compound screening technology such as (but not limited to) the ability of various dyes to change color, or fluorescent signaling/quenching in response to changes in assay conditions resulting from the activity of the polypeptides. Compound screening assays can also be based upon the ability of test compounds to modulate the interaction of the target peptide (HFE2A Polypeptide or fragments thereof) and known or discovered interacting proteins or protein receptors. Such interacting proteins can be identified by a variety of methods known in the art, including, for example, radioimmunoprecipitation, co-immunoprecipitation, use of epitope-tagged constructs in pull down experiments, co-purification by extraction and chromatography techniques, and yeast two-hybrid screening. Such interactions can be further assayed by means including but not limited to direct detection methods such as surface plasmon resonance, fluorescence with fluorophores or fluorochromes and quenching with chromophores, radiolabelled proteins, fluorescence polarization, confocal fluorescence imaging or scintillation proximity techniques. Indirect interactions may also be monitored through cell viability assays, second messenger reporting such as, G-protein coupled receptor assays, cAMP detection, nitric oxide synthase, phosphodiesterase activity, or lipid modification such as sphingomyelinase, inositol triphosphate assays.

Agents that have the effect of modulating the half-life of HFE2A Polypeptide are also useful for treating diseases of iron metabolism. By way of non-limiting example, an assay for this kind of agent comprises cells expressing a wild-type HFE2A Polypeptide wherein such polypeptides are transiently metabolically labeled during translation, contacted with a candidate compound, and the half-life of the polypeptide is determined using standard techniques. Compounds that modulate the half-life of the polypeptide are useful compounds in the present invention.

In one such assay for which the polypeptides encoded by genes disclosed herein are useful, the purified or semi-purified HFE2A polypeptide (or a fragment thereof or an epitope-tagged form or fragment thereof) is bound to a suitable support (e.g., nitrocellulose or an antibody or a metal agarose column in the case of, for example, a his-tagged form of said polypeptide). Binding to the support is preferably done under conditions that allow proteins associated with the polypeptide to remain associated with it. Such conditions may include use of buffers that minimize interference with protein-protein interactions. If desired, other proteins (e.g., a cell lysate) are added, and allowed time to associate with the polypeptide. The immobilized polypeptide is then washed to remove proteins or other cell constituents that may be non-specifically associated with it the polypeptide or the support. The immobilized polypeptide can then be used for multiple purposes. In a compound screening embodiment, such as that provided by Neogenesis Pharmaceuticals, Inc. (Cambridge, Mass.) the bound HFE2A Polypeptide will be employed in an automated ligand identification system, with low, medium or high-throughput capacity. In this case a pool of test compounds are exposed to HFE2A under conditions (i.e. buffers, temperatures, etc.) which promote specific binding of the test compounds to the protein. Compounds with non-specific binding are separated from the mixture. HFE2A/ligand complexes are then collected, and bound ligands are released and measured by mass spectrometer. A data analysis system correlates mass data with the list of compound masses included in the original test compound mixture. In an alternative embodiment, compounds can be tested for their ability to interfere with interactions between HFE2A Polypeptide and other bound molecules (which are presumably HFE2A Polypeptide interacting proteins). Compounds which can successfully displace interacting proteins are thereby identified as HFE2A Polypeptide modulating agents of the invention. Other well known protein binding assays, which use purified or semipurified target protein, can also be employed to identify test compounds with specific binding affinity for the protein.

In an alternative embodiment designed to identify HFE2A Polypeptide interacting proteins, the immobilized polypeptide is dissociated from its support, and proteins bound to it are released (for example, by heating), or, alternatively, associated proteins are released from the polypeptide without releasing the latter polypeptide from the support. The released proteins and other cell constituents can be analyzed, for example, by SDS-PAGE gel electrophoresis, Western blotting and detection with specific antibodies, phosphoamino acid analysis, protease digestion, protein sequencing, or isoelectric focusing. Normal and mutant forms of such polypeptide can be employed in these assays to gain additional information about which part of the polypeptide a given factor is binding to. In addition, when incompletely purified polypeptide is employed, comparison of the normal and mutant forms of the protein can be used to help distinguish true binding proteins. Such an assay can be performed using a purified or semipurified protein or other molecule that is known to interact with a polypeptide encoded by an HFE2A polynucleotide.

This assay may include the following steps.

1. Harvest the encoded polypeptide and couple a suitable fluorescent label to it;

2. Label an interacting protein (or other molecule) with a second, different fluorescent label. Use dyes that will produce different quenching patterns when they are in close proximity to each other versus when they are physically separate (i.e., dyes that quench each other when they are close together but fluoresce when they are not in close proximity);

3. Expose the interacting molecule to the immobilized polypeptide in the presence or absence of a compound being tested for its ability to interfere with an interaction between the two; and 4. Collect fluorescent readout data.

An alternative assay for such protein interaction is the Fluorescent Resonance Energy Transfer (FRET) assay. This assay can be performed as follows.

1. Provide the encoded protein or a suitable polypeptide fragment thereof and couple a suitable FRET donor (e.g., nitro-benzoxadiazole (NBD)) to it;

2. Label an interacting protein (or other molecule) with a FRET acceptor (e.g., rhodamine);

3. Expose the acceptor-labeled interacting molecule to the donor-labeled polypeptide in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

The description of the HFE2A provided herein teaches a wide variety of biological activities of HFE2A that may be useful for the development of low, medium or high-throughput screening assays.

One useful biological activity that works for a variety of assays is ligand binding (i.e. assays which either inhibit or enhance HFE2A binding with a ligand). The hepcidin protein (OMIM: 606464; See Roetto, A. et al. 2003. *Nature Genet.* 33: 21-22) may be a ligand of HFE2A. Those skilled in the art may find other ligands. Assays based on whole cells, cell extracts or purified proteins may be developed which measure the capacity of a test compound to inhibit or enhance HFE2A binding with a specific ligand.

Cell function assays can be designed. In these assays, a measurable cell function which is dependent on HFE2A activity can be measured to determine inhibition or enhancement by test compounds. Such functions include cell growth assays, such as where compounds are evaluated for their ability to influence axonal growth, in assays such as those described in PCT patent publication WO 02/051438, incorporated herein by reference in its entirety. In a preferred embodiment such functional assays will relate to iron metabolism and the impact of the test compound on genes and proteins pertaining to iron metabolism. In particular, the impact of the test compound could be assessed by measuring the levels or amounts or activities of such molecules as ferritin, ferroportin, hepcdin, DMT1, ferric reductase, hephaestin, transferrin, transferrin receptor 1, transferrin receptor 2, Iron Regulatory Proteins (IRPs), and the like.

Based on the presence of RGD and von Willibrand factor-like domains, HFE2A may be involved in cell-cell adhesion. An assay can be designed which relies on the biological activity of HFE2A induced adhesion, and measures a test compound's ability to modulate adhesion.

In other cell based assays, an HFE2A protein response is first calibrated. For example HFE2A may modulate release of iron by macrophages to transferrin. Or, HFE2A may modulate transport of iron across a CaCo2 membrane. Alternatively, HFE2A may induce a change in NRAMP2 iron transport behavior in an assay. One may assay for compounds which modulate these induced responses to HFE2A and thereby find a modulator of a biological activity of HFE2A. Signaling assays can be developed based on possible functions of HFE2A as a signaling molecule. Iron transport assays that may be adapted include iron uptake in an HFE-CHO cell model for duodenal crypt cells. This can be adapted to assay in 96-well plates wherein test compounds will reduce iron uptake. Similarly, test compounds may inhibit 59Fe-bound transferrin uptake in human hepatoma cells (HLF). Assays that may be suitable for adaptation include those described in Su, M. A. et al. Blood, Vol. 92 No. 6 (Sep. 15), 1998: pp. 2157-2163; Nunez M T, et al. J Nutr 1996 September; 126 (9):2151-8; Tandy S, et al. J Biol Chem 2000 Jan. 14; 275(2): 1023-9; or Feeney G P and Worwood M. Biochim Biophys Acta 2001 Apr. 23; 1538(2-3):242-51). HFE2A shares sequence similarity and similar structural domains with the human repulsive guidance molecule (RGM), (FIG. 3) and to chicken RGM-like molecule (FIG. 5). RGMs are a family of proteins involved in neural development and immune response (see WO 02/051438), though assignment of at least some of these functions to HFE2A protein must be considered doubtful, as protein and mRNA expression is not found in neural cells. In any case, related proteins are known to act locally on the cell membrane as receptors, initiating intracellular signals, and systemically as a cleaved soluble protein. Like the chicken RGM, HFE2A has a putative extracellular cleavage site suggesting that it acts as a soluble peptide. Such a soluble peptide or polypeptide could play a pivotal role in the regulation of the membrane bound form of HFE2A as is seen for a number of cytokine receptor molecules and other receptor molecules. For example, leptin and growth hormone each have a membrane bound and soluble forms of the protein. The soluble form of leptin can bind leptin in the plasma and attenuate or modulate its biological activity.

One alternate proposed mechanism of action could be that this secreted HFE2A molecule interacts with proteins on the basolateral surface of the intestinal epithelial cells, like hepcidin, and modulates the apical surface uptake of iron from diet. This interaction could be direct, at the basal surface of the intestinal cells, or via an upstream interaction resulting in modulating iron uptake. This direct or indirect effect can be assayed in a cell culture system. Alternatively, hepcidin could interact with HFE2A to modulate the relative production of the soluble compared to the membrane bound form.

An example of a compound screening assay which relies on an HFE2A induced response (i.e. an HFE2A biological activity) is a Caco2 HFE2A induced iron transport assay. Caco2 cells are a human colorectal carcinoma cell line and considered the standard for measuring intestinal absorption. These cells grown to confluence form distinct apical and basalatoral surfaces and tight junctions. Grown on permeable membranes in Transwell plate inserts, Caco2 cells become polarized with the basalatoral surface of the cell on the membrane and exposed to the B chamber solutes, while the apical side of the cell is exposed to solutes in the A chamber. This system is useful to measure active transport of iron through the intestinal epithelium from A to B, mimicking transport from the intestinal lumen through the cell to the blood. A response to HFE2A can be induced by adding HFE2A to the B (baso-lateral) chamber of the CaCo2 assay. Recombinant HFE2A can be produced in mammalian cells and the purified protein directly added to the B chamber. Alternatively, cultured cells can be transfected with HFE2A constructs and then express HFE2A protein. Appropriate cells for transfection would be HepG2 or RAW cells, human liver carcinoma cells or mouse macrophage cells, respectively. These two cell types are known to be involved in iron metabolism, and likely express HFE2A. The media from these transfected "donor" cells containing HFE2A can now be applied to the B chamber of the Caco2 cells, "acceptor" of the conditioned media, and iron absorption from the A chamber can be monitored. The transfected donor cells could also be grown on the bottom of the B chamber surface, thus directly releasing HFE2A into the B chamber, within millimeters from the basal surface of the acceptor cells.

Whether HF2A acts as a receptor, intracellular signal molecule or secreted protein or combinations of these mechanisms, this multicellular communication system can be applied to measure an HFE2A induced response. The assay may measure iron transport, iron uptake from the A chamber, iron absorption and/or cell secretion of iron to the B chamber. This cell communication system can thereafter be applied to primary drug compound screening for iron modulation in intestinal absorption.

Using whole cells or cell extracts, assays can be developed for compounds which increase or decrease GPI cleavage or secretion of HFE2A or for compounds which increase or decrease N-glycosylation of HFE2A. Such compounds or agents that modulate the rate of GPI release of HFE2A could play key role in modulation of HFE2A activity and thus may serve as novel compounds for further development for the treatment of a disorder of iron metabolism. Assays that measure compounds which modulate post-translational modifiers of HFE2A can be used to identify potential therapeutic agents.

Some assays preferably employ purified or semi-purified HFE2A protein assays. This protein may be the GPI-linked form, or the cleaved, soluble form. $I^{125}$ labelled HFE2A may be useful for these assays. Such assays include aggregation, assays which are designed based on the tendency of HFE2A to aggregate or homodimerize via the RGD or von Willibrand factor-like domains. In this assay, compounds are tested for their ability to enhance or prevent aggregation of homophilic dimerization domains. In this case, the protein-protein interaction assays above can use two pools of HFE2A, each labelled with a different fluorophore. In some embodiments a GPI-cleaved form of HFE2A may be used with the GPI-linked form. An alternate semi-purified format includes yeast 2-hybrid and/or phage display formats, wherein HFE2A binding regions are incorporated into both bait and prey vectors. This format would provide a moderately high throughput screening assay, suitable for radioimmunoassay or plate format.

In addition it is to be noted that HFE2A may interact with other known proteins of the iron metabolic pathway: Transferrin, Tf receptor, Hfe, hepcidin, p97 or other iron transporters, and receptors thereof. This interaction is a useful activity which may be used as the basis for a screening assay.

Additionally, drug screening assays can also be based upon polypeptide functions deduced upon antisense interference with the gene function. Intracellular localization of HFE2A, or effects which occur upon a change in intracellular localization of such proteins, can also be used as an assay for drug screening.

The invention also claims recombinant cells engineered to express a polynucleotide or polypeptide as disclosed herein. The gene disclosed herein as being involved in HFE2A in an animal can be used, or a fragment thereof can be used, as a tool to express a protein, where such genes encode a protein, in an appropriate cell in vitro, or can be cloned into expression vectors which can be used to produce large enough amounts of protein to use in in vitro assays for drug screening. Expression systems which may be employed include baculovirus, herpes virus, adenovirus, adeno-associated virus, bacterial systems, and eucaryotic systems such as CHO cells. Naked DNA and DNA-liposome complexes can also be used. The invention thus claims recombinant cell lines containing polynucleotides and polypeptides of the invention.

Such recombinant cells may be used in transcription assays for analyzing the levels of transcription of HFE2A Gene or a suitable reporter gene after contacting said cells with agents that may have therapeutic properties. The levels of gene transcription can be quantified by Northern blot analysis or RT-PCR, or, alternatively, by measuring the amount of protein produced, by one of a number of methods known in the art, or by measuring the levels of biological activity of polypeptides encoded thereby or other genes. In this way, the gene transcription can serve as a marker, indicative of the physiological response of the cells to the agent. Accordingly, this response state may be determined before, and at various points during, treatment of the individual with the agent.

Recombinant cell lines are also preferred for the preparation of purified protein, if a purified protein assay is desired. Those skilled in the art are capable of producing recombinant cell lines and extracting protein fractions containing highly purified proteins. These samples can be used in a variety of binding assays to identify compounds which interact with the proteins. Compounds that interact are therapeutic agents of the invention, or analogs thereof.

Target selectivity is an important aspect of the development of therapeutic agents. The present invention specifically contemplates the identification of chemical agents, especially small organic molecules or protein or peptide molecules, that agonize or antagonize the transcription of HFE2A Gene, as defined herein, or the activity of the HFE2A Polypeptide (such as SEQ ID NO: 10-12 from humans) or HFE2A fragments (such as SEQ ID NO: 13-31) encoded thereby, with preferably high specificity and that have preferably little or no effect on other genes and/or polypeptides.

Thus, in one such preferred embodiment, the methods disclosed herein for identifying an agent that modulates, preferably inhibits, expression of a gene corresponding to HFE2A, preferably having the sequence of SEQ ID NO: 1-9 from humans, or on the activity of a polypeptide encoded thereby, comprises first identifying such agent and then testing such agent for effects on expression or activity of at least one other gene or polypeptide, preferably a gene or polypeptide with important physiological consequences that are preferably not disturbed by therapeutic intervention, and demonstrating little or no effect.

In another aspect, the invention provides a method for computationally identifying a compound of the invention. The method involves (a) determining the crystal structure of an active site of a HFE2A Polypeptide protein (i.e. through x-ray crystallography or other techniques); and (b) through computational modeling, identifying a compound which interacts with the active site, thereby identifying a compound, or its analog, as a compound which is useful for modulating the activity of such a polypeptide. This process is sometimes referred to as in silico screening. Sophisticated software for testing the probability of test compounds to interact with the target protein, which can test tens of millions of computer generated compounds, is available to those skilled in the art.

Potential therapeutic compounds identified using the methods of the invention are usually tested in animal model systems to confirm the putative efficacy. Thus, in a further aspect, the present invention relates to a method for identifying a therapeutic agent, comprising:

a) administering to an animal an agent found to have activity using an assay or screening method as disclosed herein or an agent derived by any other means, and b) detecting in said animal a change in iron metabolism due to said administering, thereby identifying an agent for the treatment a disease of iron metabolism.

Those skilled in the art are aware that typical measurements of iron metabolism that may be modulated in animal models (i.e., as a result of treatment with a potential therapeutic agent) include transferrin saturation, hepcidin levels, radioactive iron uptake in the gut, liver iron content, whole body iron content, anemia indices. Specialized mouse models for study include anemic mice, iron overload mice, hemochromatosis mice (hfe/hfe), Hpx mice (hypotransferrinemic mouse), and others.

In a further aspect, the present invention relates to a method for treating a condition in an animal afflicted with a disease of iron metabolism comprising administering to said animal an effective amount of an agent first identified by an assay method of the invention. Preferably, said animal is a human patient, such as a patient afflicted with a disease of iron metabolism.

The screening assays of the invention thus simplify the evaluation, identification and development of therapeutic agents for the treatment of diseases of iron metabolism.

The invention also includes antibodies and immuno-reactive substances which target, interact with or bind to hemojuvelin, HFE2A Polypeptide or epitopes thereof. Polypeptides encoded by the polynucleotides disclosed herein can be used as an antigen to raise antibodies, including monoclonal antibodies. Such antibodies will be useful for a wide variety of purposes, including but not limited to, therapeutic agents, functional studies, drug screening assays, and/or diagnostic agents. Monitoring the influence of agents (e.g., small organic compounds) on the expression or biological activity of the HFE2A polypeptides identified according to the invention can be applied not only in basic drug screening, but also in clinical trials. For example, the effectiveness of an agent determined by a screening assay as described herein to increase or decrease gene transcription, protein levels, or biological activity can be monitored in clinical trails of subjects exhibiting symptoms of diseases of iron metabolism due to inadequate gene transcription, protein levels, or biological activity. Alternatively, the effectiveness of an agent determined by a screening assay as described herein to increase or decrease gene transcription, protein levels, or biological activity can be monitored as part of the theapeutic response as a surrogate marker of treatment efficacy in subjects exhibiting symptoms of diseases of iron metabolism. Such a pharmacogenomic approach will allow for accurate application of the intended therapeutic to those best suited and most likely to respond based on measurement and diagnosis of levels and or activity of HFE2A as well as other key iron-related proteins.

Alternatively, the effectiveness of an agent determined by a screening assay to modulate transcription of HFE2A Gene, as well as structurally and functionally related genes, including genes with high homology thereto, and including protein levels, or biological activity can be monitored in clinical trials of subjects exhibiting decreased altered gene transcription, protein levels, or biological activity. In such clinical trials, the transcription or activity of the genes or polypeptides disclosed herein and, preferably, other genes that have been implicated in, for example, iron metabolism, can be used to ascertain the effectiveness of a particular drug.

In a preferred embodiment, the present invention provides a method for monitoring the effectiveness of treatment of a subject with an agent (e.g., an agonist, antagonist, peptidomimetic, protein, peptide, antibody, nucleic acid, small molecule, ribozyme, antisense molecule, siRNA, or other drug candidate identified by the screening assays described herein) including the steps of (i) determining that a patient requires treatment for an iron metabolism disease or disorder; (ii) administering an effective amount of an agent identified using one of the screening assays disclosed herein; (iii) ascertaining an improvement in iron metabolism following said administration and (vi) altering the administration of the agent to the subject accordingly. For example, increased administration of the agent may be desirable to decrease the expression or activity of gene or encoded polypeptide, i.e., to increase the effectiveness of the agent.

Where the patient is non-human, biopsy samples can be taken to show a decrease in gene transcription, such as by measuring levels of protein, mRNA, or genomic DNA post-administration samples and comparing the level of expression or activity of said protein, mRNA, or genomic DNA in the pre-administration sample with that of the corresponding post administration sample or samples, thereby showing the effects of drug administration on one or more of the genes disclosed herein and concomitant reduction in problems with iron metabolism.

Where the patient is human, appropriate tissue samples including but not limited to blood, and urine, can be taken to show a decrease in gene transcription, such as by measuring levels of protein, mRNA, or genomic DNA post-administration samples and comparing the level of expression or activity of said protein, mRNA, or genomic DNA in the pre-administration sample with that of the corresponding post administration sample or samples, thereby showing the effects of drug administration on one or more of the genes disclosed herein and concomitant reduction in problems with iron metabolism.

Purified or semi-purified HFE2A protein, or fragments thereof, or proteins corresponding to HFE2A, and any biochemically modified versions thereof, are themselves therapeutic agents of the invention. This includes all potential sized fragments of the protein which could be generated based on the bioinformatic prediction of cleavage sites including GPI cleavage, furin cleavage, asp-pro RGM cleavage site and the N-terminal signal peptide cleavage site. Recombinant or non-recombinant forms of these proteins or fragments can be administered to persons in need thereof for the treatment of disorders, such as diseases of iron metabolism. Those skilled in the art are familiar with techniques for generating such agents, and for determining conditions of administration.

Specific compounds which will modulate the gene expression or gene transcript levels in a cell of HFE2A include antisense nucleic acids, ribozymes and other nucleic acid compositions which specifically hybridize with the HFE2A gene (including exons or introns of such genes, promoters, 3'-tails, and the like). These specific compounds are compounds of the invention, and are useful for treating the diseases discussed previously. Design and manufacturing of such compounds are well known to those skilled in the art.

Specific compounds which modulate the activity of HFE2A include antibodies (polyclonal or monoclonal) and modified antibodies or fragments of antibodies which specifically bind to an epitope of said polypeptide. These specific compounds are compounds of the invention, and are useful for treating the diseases previously discussed. Design and manufacturing of such compounds are well known to those skilled in the art. In particular, humanized antibodies tend to be preferred, such as those generated using techniques provided by Abgenix, Inc. (Freemont, Calif.), Medarex, Inc. (Princeton, N.J.), Protein Design Labs, Inc. (Freemont, Calif.), Genentech (South San Francisco, Calif.), and others.

Specific compounds which modulate the activity of HFE2A include proteins and peptides or fragments thereof. These specific compounds are compounds of the invention, and are useful for treating the diseases previously discussed. Design and manufacturing of such compounds are well known to those skilled in the art. In particular, Bachem (Torrance, Calif.), Cambridge Peptides (Cambridge, UK), Biopeptide Company (San Diego, Calif.), and others.

Specific compounds which modulate the activity of HFE2A in the body include gene therapy vectors comprising all or a part of the HFE2A gene sequence or mutant HFE2A sequence. As is well known to those skilled in the art, gene therapy allows the delivery of HFE2A in an organism to cells where it is taken up and expressed, thus changing the level or amount of HFE2A Polypeptide protein in such cell. These vectors thereby modulate the activity of HFE2A in the body and are useful for the therapeutic indications disclosed herein.

Specific compounds which modulate the activity of HFE2A in the body include small organic molecules. Such compounds may be naturally occurring, or they may be synthetic. Collections and combinatorial libraries of such compounds are widely available from commercial sources. As know to those skilled in the art, a screening assay, such as the assays disclosed in the instant specification, can be easily adapted to identify therapeutic agents which have the desired HFE2A modulating ability. Agonists, antagonists, or mimetics found to be effective at reducing disorders of iron metabolism may be confirmed as useful in animal models (for example, mice, chimpanzees, etc.). In other embodiments, treatment with a compound of the invention may be combined with other therapeutic agents to achieve a combined, possibly even synergistic, effect.

Candidate modulators may be purified (or substantially purified) molecules or may be one component of a mixture of compounds (e.g., an extract or supernatant obtained from cells). In a mixed compound assay, gene or protein expression is tested against progressively smaller subsets of the candidate compound pool (e.g., produced by standard purification techniques, such as HPLC or FPLC) until a single compound or minimal compound mixture is demonstrated to modulate gene or protein activity or expression in a manner having therapeutic effects.

Lead Optimization and Analog Development and Selection

In general, novel drugs having therapeutic properties are identified from libraries, possibly large libraries, of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

De-replication (e.g., taxonomic de-replication, biological de-replication, and chemical de-replication, or any combination thereof) or the elimination of replicates or repeats of materials already known for their therapeutic activities may be employed whenever possible.

When a crude extract is found to have therapeutic activities, further fractionation of the positive lead extract is possible to isolate chemical constituent responsible for the observed effect. Thus, the goal of the extraction, fractionation, and purification process is the careful characterization and identification of a chemical entity within the crude extract having such therapeutic activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for the treatment of pathogenicity are chemically modified according to methods known in the art. Compounds identified as being of therapeutic value are subsequently analyzed using any standard animal model of an iron metabolism disorder known in the art.

In general, these screening methods provide a ready means for selecting either natural product extracts or synthetic compounds of interest from a large population (i.e. a chemical library, for example, one produced by combinatorial means) which are further evaluated and condensed to a few active core structures. Multiple analogs of such core structures may be developed and tested to identify those preferred analogs which have improved characteristics as therapeutic agents.

Improved analogs may also include compounds with improved stability, biodistribution, pharmacokinetics or other desirable features for therapeutic agents which are not directly related to modulation of the therapeutic target. In a preferred embodiment, the improved analog of the invention is effectively delivered, either by physiological means or assisted means, to cells of the body expressing the HFE2A Polypeptide protein or the improved analog may target the HFE2A protein in the plasma directly. Analog compounds are systematically screened to evaluate whether they modulate the identified biological activity and those that effectively do so are then therapeutic agents, or further analogs thereof, according to the invention.

Therapeutic Agents and Uses Thereof

Those skilled in the art are familiar with the necessary steps for pre-clinical and human clinical trials which are used to establish efficacy and safety of the new chemical entities and compounds first identified by the invention for use in treating the diseases mentioned herein.

Compounds first identified as useful therapeutic agents using one or more of the assays of the invention may be administered with a pharmaceutically-acceptable diluent, carrier, or excipient, in unit dosage form. Conventional pharmaceutical practice may be employed to provide suitable formulations or compositions to administer such compositions to patients. Although oral administration is preferred, any appropriate route of administration may be employed, for example, intravenous, parenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, *Remington: The Science and Practice of Pharmacy*, (19th ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

Combination therapies are also contemplated by the inventors. An therapeutic agent identified by one of the screening methods disclosed herein may be administered along with another agent intended to treat a coincident conditions, such as where therapeutic and antitumor agents are given together or contemporaneously. Importantly, one preferred embodiment is for the use of HFE2A therapeutic agent in combination with erythropoietin for the treatment of anemia, in particular Anemia of Chronic Disease.

The present invention also relates to a process that comprises a method for producing a product, such as by generating test data to facilitate identification of such product, comprising identifying an agent according to one of the disclosed processes for identifying such an agent (i.e., the therapeutic agents identified according to the assay procedures disclosed herein) wherein said product is the data collected with respect to said agent as a result of said identification process, or assay, and wherein said data is sufficient to convey the chemical character and/or structure and/or properties of said agent. For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

In accordance with the foregoing, the present invention relates to a method for producing test data with respect to the modulation of HFE2A gene expression by a compound, comprising:

(a) a genetic construct comprising a reporter gene operably linked to an HFE2A promoter under conditions supporting expression of said reporter gene;

(b) determining a change in expression of said reporter gene as a result of said contacting, wherein said change shows modulation, and (c) producing test data with respect to the gene modulating activity of said test compound based on a change in expression of the determined genes indicating gene modulating activity.

In another such embodiment, the present invention relates to a method for producing test data with respect to the modulation of an HFE2A polypeptide activity by a compound, comprising:

(a) contacting a test compound with an HFE2A polypeptide and under conditions promoting an activity of said HFE2A polypeptide;

(b) determining a change in activity of said polypeptide as a result of said contacting, wherein said change shows modulation, and (c) producing test data with respect to the HFE2A polypeptide modulating activity of said test compound based on a change in an HFE2A polypeptide activity indicating modulating activity.

Diagnostics and Pharmacogenomics

In a further embodiment, the invention relates to diagnostic and pharmacogenomic compounds, kits and methods. This aspect relates to analysis of HFE2A protein or cleavage products thereof for the diagnosis, including prognosis of onset or severity of onset, of juvenile hemochromatosis, adult onset hemochromatosis, a disorder of iron metabolism, or in the differential diagnosis between anemia of chronic diseases and iron deficiency anemia, or in the selection of a therapeutic agent for an individual, or ongoing monitoring of the efficacy of the intended therapeutic, or use to modify the dose of the intended therapeutic or the selection of patient subset who will most likely benefit from said therapy (i.e. pharmacogenomics). It also relates to the use of HFE2A diagnosis to classify individuals as having or at risk of having a disease of iron metabolism.

In a particular example, nucleic acid analysis can be used to identify the HFE2A mutations disclosed herein, thus confirming the diagnosis of juvenile hemochromatosis.

Using the nucleic acid sequences disclosed in this invention, both the wild-type (non-disease associated) sequences (SEQ ID No. 1-9) and the disease associated (mutated) sequences (SEQ ID Nos. 14, 16, and 18), those skilled in the art are capable of developing numerous different types of nucleic acid diagnostic methods, compounds and kits. Techniques include DNA sequencing, hybridization probing, single stranded conformational analysis, PCR based techniques such as mismatch amplification, and myriad other well known methods. All such analysis can be performed on a small sample of blood, plasma, serum, urine, saliva, cerebral spinal fluid, skin, liver and fractions thereof. provided by the individual.

Alternatively, using the protein sequences disclosed in this invention (SEQ ID No.—10-31) protein based analyses such as antibody based assays (Elisa, Radioimmunoassay and the like) can be employed to identify the level, amount or activity of an HFE2A and/or fragment thereof. In another embodiment, a protein of iron metabolism found in a sample obtained from an individual can be used in assays, either alone or in conjunction with the foregoing assays, to detect, prognose, diagnose, or for patient selection and stratification, or monitor diseases of iron metabolism. Such "protein of iron metabolism" can include but not limited to hepcidin, ferroportin, HFE, TFR1, TFR2, soluble transferring reporter 1, haptoglobin, and DMT1. Such "samples" can include blood, plasma, serum, urine, saliva, cerebral spinal fluid, skin, liver and fractions thereof. Other means of evaluation of HFE2A cleavage product could also be employed including use of proteomic technologies, western blots, immunoprecipitation assays, gel diffusion, immunodiffusion assays, fluorescent immunoassays, but to name a few.

In a particular example, such an assay is carried out by contacting a sample derived from an individual with an anti-HFE2A antibody or anti-HFE2A cleavage product antibody under conditions such that immunospecific binding can occur, and detecting or measuring the amount of immunospecific binding by the antibody, wherein an aberrant level of HFE2A or HFE2A cleavage product is an indication of a disease state. By "aberrant levels", is meant increased or decreased levels relative to that present, or a standard level representing that present, in an analogous sample from an individual not having the disorder.

According to one embodiment of the present invention, the HFE2A cleavage products, derivatives or analogs thereof may be used as an immunogen. Such antibodies include but are not limited to polyclonal, monoclonal, chimeric, single chain, Fab fragments, and an Fab expression library. Various procedures known in the art may be used for the production of the polyclonal antibodies to HFE2A cleavage products of the present invention. Various host animals can be immunized by injection with the native HFE2A cleavage product or a synthetic version, or derivative or analog thereof. There are many well known methods in the art for the preparation of monoclonal, for example, the hybridoma technique originally developed by Kohler and Milstein (1975, Nature 256:495-497). According to the invention, human antibodies may be used and can be obtained by using human hybridomas (Cote et al., 1983. Proc. Natl. Acad. Sci. U.S.A. 80:2026-2030). Techniques for the production of chimeric antibodies (Morrison et al., 1984. Proc. Natl. Acad. Sci. U.S.A. 81:6851-6855) can be adapted to splice together a mouse antibody specific for a HFE2A cleavage product with genes from a human antibody molecule.

According to the invention, techniques described for the production of single chain antibodies (U.S. Pat. No. 4,946,778) can be adapted to produce, for example, HFE2A cleavage product-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for HFE2A cleavage products. Additionally, Antibody fragments which contain the idiotype of the molecule can be generated by known techniques.

As Juvenile Hemochromatosis is a potentially lethal condition if missed and can be easily cured with phlebotomy if recognized in a timely fashion, it is suggested that early newborn or neonatal or childhood screening for Juvenile Hemochromatosis may be warranted. Such screening could be performed by examining the HFE2A gene, mRNA or protein. In one embodiment, the HFE2A gene would be sequenced or alternatively specific SNPs would be interrogated. In another preferred embodiment, the protein levels of HFE2A or the activity of HFE2A protein would be evaluated either alone or in conjunction with a panel of other iron related proteins/genes. In particular, HFE2A protein or gene would be examined in conjunction with hepcidin protein or gene.

Gene transcription, both comparable and absolute, as well as biological activity, and mutational analysis can each serve as a diagnostic tool for a disease of iron metabolism; thus determination of the amount of HFE2A mRNA can be used to diagnose the presence or absence of a mutation correlated with such a disease.

Based on the instant invention, those skilled in the art will also be able to develop other biochemical, chemical and diagnostic assays of HFE2A mutation which are suitable for use with animal tissue samples.

A valuable embodiment of the invention will be to use the diagnostic assays to classify patients having or at risk of having a disease of iron metabolism. There are many risk factors for diseases of iron metabolism, such as enhanced serum ferritin levels, transferrin receptor saturation, or identification of a mutation in a gene for hemochromatosis (i.e. the Hfe gene). Not all of these risk factors lead to the development of a disease of iron metabolism. Using the teaching of the invention, it is now possible to take patients at risk of having a disease of iron metabolism based on a known risk factor and further assessing them for mutations in HFE2A, wherein a mutation in HFE2A (in one or both copies of the gene) indicates a statistically greater chance of developing the disease of iron metabolism. This discovery particularly aids in diagnosis and prognosis of the risk of adult onset hemochromatosis, which is a condition that is not fully penetrant. Thus other factors besides the HFE mutation status contribute to the severity and onset of adult hemochromatosis. HFE2A mutations, at least in part, may contribute to the clinical manifestation of adult hemochromatosis and therefore, interogation for HFE2A mutations or protein pertubations, will provide additional insight into prognostic and diagnostic issues surrounding adult onset hemochromatosis.

What follows is an example of the diagnostic benefit of HFE2A in relation to adult onset hemochromatosis. Protein analysis used to identify the level, amount or activitiy of HFE2A or fragments thereof and as disclosed herein, could be used to predict onset or severity of adult hemochromatosis. Adult hemochromatosis displays a wide variability in clinical penetrance. In some human subjects homozygous for HFE mutations there is early onset of a severe phenotype, while in other subjects homozygous for HFE mutations, they remain clinically normal. Assessment of HFE2A gene may be informative for which patients will manifest adult disease and which ones will remain relatively symptom free.

Pharmacogenomics deals with clinically significant hereditary variations in the response to drugs due to altered drug disposition and abnormal action in affected persons (Eichelbaum, M., Clin. Exp. Pharmacol. Physiol., 23:983-985, 1996; Linder, M. W., Clin. Chem., 43:254-266, 1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). Altered drug action may occur in a patient having a polymorphism (e.g., an single nucleotide polymorphism or SNP) in promoter, intronic, or exonic sequences of HFE2A Gene. Thus by determining the presence and prevalence of polymorphisms allow for prediction of a patient's response to a particular therapeutic agent.

This pharmacogenomic analysis can lead to the tailoring of drug treatments according to patient genotype, including prediction of side effects upon administration of therapeutic agents, particularly therapeutic agents for treating disorders disclosed in this specification. Pharmacogenomics allows for the selection of agents (e.g., drugs) for therapeutic or prophylactic treatment of an individual based on the genotype of the individual (e.g., the genotype of the individual is examined to determine the ability of the individual to respond to a particular agent).

Diagnostics employing a gene or protein corresponding to HFE2A Gene (HFE2A) can also be useful in selecting patients for clinical trials of a potential therapeutic agent. Patients can be stratified according to the DNA or protein sequence of HFE2A Gene and their response to drug treatment can be evaluated. Such stratification can greatly reduce the number of patients required to establish efficacy for a potential therapeutic agent.

Diagnostics employing a gene or protein corresponding to HFE2A Gene (HFE2A) can also be useful in selecting patients for use of a potential therapeutic agent. Patients can be stratified according to the DNA or protein sequence of HFE2A Gene and those patients with a particular HFE2A profile could potentially benefit the most from the intended therapeutic. Such stratification can greatly improve efficacy for a potential therapeutic agent. In one embodiment, the intended therapeutic will be an HFE2-related agent. In this situation, diagnostic evaluation of HFE2A will predict who should be treated with the HFE2A therapeutic and who should not be treated.

The invention thus comprises compounds, reagents and kits which are designed to identify the presence or absence of mutations in the HFE2A gene.

Additional Information about the Sequences Disclosed in the SEQ ID Listing in this Specification:

LOC148738 Exons

Exons 1, 3a, 3b and 4 may also be found at Gene ENSG00000168509 (Ensembl) and REFSEQ NM_145277.1 (NCBI). Exon 2 may be inferred from an ensembl prediction based on the sequence AK098165.1.

To simplify sequence searching, exon sequence coordinates are provided below based on the NCBI 31 assembly of the human genome. The SEQ ID NOs for these are:

SEQ ID NO. 1—Exon1 ENSE00001155188 Start: 142000393, End:142000541 Chr: 1

SEQ ID NO. 2—Exon2 Start: 142001790, End: 142001993 Chr:1

SEQ ID NO. 3—Exon3a ENSE00001155182 Start: 142002394, End: 142002430 Chr:1

SEQ ID NO. 4—Exon3b ENSE00001277320 Start: 142002394, End: 142002953 Chr: 1

SEQ ID NO. 7—Transcript 2 ENST00000317920 Exons 1, 3a, 4, translation_start: 208

SEQ ID NO. 8—Transcript 3 Exons 1, 3b, 4 translation_start: 392

SEQ ID NO. 9—Transcript 4 Exons 1, 2, 3b, 4 translation_start: 257

LOC148738 Translated Proteins

Protein1 is the protein translation of Transcript 1 and Transcript 2 and is similar to the Ensembl protein ENSP00000320072 and the NCBI protein NP_660320.1. Protein 2 is the protein translation of Transcript 2 and may be found in the protein translation of AK098165.1. Protein 3 is similar to the predicted Ensembl Protein ENSP00000304614. SEQ ID NOs are as follows:

SEQ ID NO. 10-Protein1 ENSP00000320072 Translated from Transcript 1 and Transcript 2

SEQ ID NO. 11-Protein 2—Translated from Transcript 3

SEQ ID NO. 12-Protein 3 ENSP00000304614 Translated from Transcript 4

HFE2A Predicted Cleavage Products

For SEQ ID Nos. 13-26, the amino acid sequences for the predicted cleavage products based on the analysis of the 426 aa gene product (Protein 3):

SEQ ID NO. 13—N-terminal signal peptide

SEQ ID NO. 14—C-terminal signal peptide

SEQ ID NO. 15—N-terminal Asp/Pro peptide

SEQ ID NO. 16—N-terminal Asp/Pro peptide (minus N-terminal signal peptide)

SEQ ID NO. 17—C-terminal Asp/Pro peptide

SEQ ID NO. 18—N-terminal Furin peptide

SEQ ID NO. 19—Asp/Pro to Furin peptide

SEQ ID NO. 20—C-terminal Furin peptide

SEQ ID NO. 21—C-terminal GPI peptide

SEQ ID NO. 22—N-terminal GPI anchor peptide

SEQ ID NO. 23—Furin to GPI anchor peptide

SEQ ID NO. 24—Asp/Pro to GPI anchor peptide

SEQ ID NO. 25—Signal to GPI anchor peptide

SEQ ID NO. 26—Signal to Furin peptide

The amino acid sequence for the predicted cleavage products based on the analysis of the 200 aa gene product (Protein 1) have SEQ ID NOs as follows:

SEQ ID NO. 27—N-terminal Furin peptide

SEQ ID NO. 28—N-terminal GPI anchor peptide

The amino acid sequence for the predicted cleavage products based on the analysis of the 313 aa gene product (Protein 2) have SEQ ID NOs as follows:

SEQ ID NO. 29—N-terminal Asp/Pro peptide

SEQ ID NO. 30—N-terminal Furin peptide

SEQ ID NO. 31—N-terminal GPI anchor peptide

Those skilled in the art will be familiar with numerous variations of the compositions and methods disclosed above, all of which are encompassed by the claims further set out below. All publications referred to in this specification are hereby incorporated by reference in their entireties, though no such publication is hereby admitted to be a prior art reference.

What is claimed is:

1. An isolated polypeptide, wherein said polypeptide consists of an amino acid sequence selected from the group consisting of SEQ ID NO: 20 and 25, or comprises the amino acid sequence of SEQ ID NO: 15, wherein said polypeptide has the biological function of modulation of iron transport across a cell membrane of a cell that transports iron.

2. The isolated polypeptide of claim 1, wherein said amino acid sequence is SEQ ID NO: 25.

3. The isolated polypeptide of claim 1, wherein said polypeptide has a molecular weight between about 7 kDa and 43 kDa.

4. A composition for treating a disease of iron metabolism comprising a therapeutically effective amount of a polypeptide of any one of claims 1, 2 or 3 in a pharmaceutically acceptable carrier.

5. A method for treating a disease of iron metabolism comprising administering to a patient in need thereof a therapeutically effective amount of a composition of claim 4.

6. The method of claim 5, wherein said disease is Anemia of Chronic Disease, hemochromatosis, or juvenile hemochromatosis.

7. The isolated polypeptide of claim 1, wherein said cell is selected from the group consisting of a macrophage, inflammatory cell, liver cell, hepatocyte, intestinal cell, hematopoietic cell, pancreatic cell, skeletal muscle cell, or a cell of the nervous system.

8. The isolated polypeptide of claim 1, wherein said modulation of iron transport across a cell membrane results in release of iron by said cell.

9. The isolated polypeptide of claim 1, wherein said iron transport across a cell membrane results in iron uptake by said cell.

10. The isolated polypeptide of claim 9, wherein said cell is a recombinant cell that has been engineered to express a polypeptide of claim 1.

11. The isolated polypeptide of claim 9, wherein said cell is a Caco2 cell.

12. The isolated polypeptide of claim 9, wherein said cell is a macrophage.

13. The isolated polypeptide of claim 7, wherein said cell is a hepatocyte.

14. The isolated polypeptide of claim 7, wherein said cell is an intestinal cell.

15. The isolated polypeptide of claim 1, wherein said cell is a CHO.

16. An isolated polypeptide consisting of the amino acid sequence of SEQ ID NO: 25.

17. An isolated polypeptide consisting of the amino acid sequence of SEQ ID NO: 20.

18. An isolated polypeptide consisting of the amino acid sequence of SEQ ID NO:15.

* * * * *

SEQUENCE LISTING

<160> NUMBER OF SEQ ID NOS: 53

<210> SEQ ID NO 1
<211> LENGTH: 149
<212> TYPE: DNA
<213> ORGANISM: Homo sapiens

<400> SEQUENCE: 1
cttctctggt tccctgacct cagtgagaca gcagccggcc tggggacctg ggggagacac      60
ggaggacccc ctggctggag ctgacccaca gagtagggaa tcatggctgg agaattggat     120
agcagagtaa tgtttgacct ctggaaaca                                       149

<210> SEQ ID NO 2
<211> LENGTH: 204
<212> TYPE: DNA
<213> ORGANISM: Homo sapiens

<400> SEQUENCE: 2
ccaaatttct tttttcagtc acttacaggg cttccggtca aaattcacta ggtaggaggg      60
tcatcagctg ggaagaaccg gcgcctggga aacctggctg ataggtatg ggggagccag      120 gccagtcccc tagtcccagg tcctcccatg gcagtccccc aactctaagc actctcactc     180
tcctgctgct cctctgtgga catg                                            204

<210> SEQ ID NO 3
<211> LENGTH: 37
<212> TYPE: DNA
<213> ORGANISM: Homo sapiens

<400> SEQUENCE: 3
ctcattctca atgcaagatc ctccgctgca atgctga                              37

<210> SEQ ID NO 4
<211> LENGTH: 560
<212> TYPE: DNA
<213> ORGANISM: Homo sapiens

<400> SEQUENCE: 4
ctcattctca atgcaagatc ctccgctgca atgctgagta cgtatcgtcc actctgagcc      60
ttagaggtgg gggttcatca ggagcacttc gaggaggagg aggaggaggc cggggtggag     120
gggtgggctc tggcggcctc tgtcgagccc tccgctccta tgcgctctgc actcggcgca     180
ccgcccgcac ctgccgcggg gacctcgcct tccattcggc ggtacatggc atcgaagacc     240
tgatgatcca gcacaactgc tcccgccagg gccctacagc ccctcccccg ccccggggcc     300
ccgcccttcc aggcgcgggc tccggcctcc ctgccccgga cccttgtgac tatgaaggcc     360
ggttttcccg gctgcatggt cgtccccggg ggttcttgca ttgcgcttcc ttcgggacc      420 cccatgtgcg cagcttccac catcactttc acacatgccg tgtccaagga gcttggcctc     480
tactggataa tgacttcctc tttgtccaag ccaccagctc ccccatggcg ttggggggcca    540 acgctaccgc cacccggaag                                                 560

<210> SEQ ID NO 5
<211> LENGTH: 1230
<212> TYPE: DNA
<213> ORGANISM: Homo sapiens

<400> SEQUENCE: 5

```
ctcaccatca tatttaagaa catgcaggaa tgcattgatc agaaggtgta tcaggctgag      60
gtggataatc ttcctgtagc cttttgaagat ggttctatca atggaggtga ccgacctggg    120
ggatccagtt tgtcgattca aactgctaac cctgggaacc atgtggagat ccaagctgcc    180
tacattggca caactataat cattcggcag acagctgggc agctctcctt ctccatcaag    240
gtagcagagg atgtggccat ggccttctca gctgaacagg acctgcagct ctgtgttggg    300
gggtgccctc caagtcagcg actctctcga tcagagcgca atcgtcgggg agctataacc    360
attgatactg ccagacggct gtgcaaggaa gggcttccag tggaagatgc ttacttccat    420
tcctgtgtct ttgatgttttt aatttctggt gatcccaact ttaccgtggc agctcaggca    480
gcactggagg atgcccgagc cttcctgcca gacttagaga agctgcatct cttcccctca    540
gatgctgggg ttcctctttc ctcagcaacc ctcttagctc cactcctttc tgggctcttt    600
gttctgtggc tttgcattca gtaaggggac catcagtccc attactagtt tggaaatgat    660
ttggagatac agattggcat agaagaatgt aaagaatcat taaaggaagc agggcctagg    720
agacacgtga acaatgaca ttatccagag tcagatgagg ctgcagtcca gggttgaaat    780
tatcacagaa taaggattct gggcaaggtt actgcattcc ggatctctgt ggggctcttc    840
accaattttt ccagcctcat ttatagtaaa caaattgttc taatccattt actgcagatt    900
tcacccttat aagtttagag gtcatgaagg ttttaatgat cagtaaagat ttaagggttg    960
agatttttaa gaggcaagag ctgaaagcag aagacatgat cattagccat aagaaactca   1020
aaggaggaag acataattag ggaaagaagt ctatttgatg aatatgtgtg tgtaaggtat   1080
gttctgcttt cttgattcaa aaatgaagca ggcattgtct agctcttagg tgaagggagt   1140
ctctgctttt gaagaatggc acaggtagga cagaagtatc atccctaccc cctaactaat   1200
ctgttattaa agctacaaat tcttcacacc                                      1230
```

<210> SEQ ID NO 6
<211> LENGTH: 1379
<212> TYPE: DNA
<213> ORGANISM: Artificial Sequence
<220> FEATURE:
<223> OTHER INFORMATION: Putative HFE2A cDNA from Homo sapiens

<400> SEQUENCE: 6

```
cttctctggt tccctgacct cagtgagaca gcagccggcc tggggacctg ggggagacac     60
ggaggacccc ctggctggag ctgacccaca gagtagggaa tcatggctgg agaattggat    120
agcagagtaa tgtttgacct ctggaaacac tcaccatcat atttaagaac atgcaggaat    180
gcattgatca gaaggtgtat caggctgagg tggataatct tcctgtagcc tttgaagatg    240
gttctatcaa tggaggtgac cgacctgggg gatccagttt gtcgattcaa actgctaacc    300
ctgggaacca tgtggagatc caagctgcct acattggcac aactataatc attcggcaga    360
cagctgggca gctctccttc tccatcaagg tagcagagga tgtggccatg gccttctcag    420
ctgaacagga cctgcagctc tgtgttgggg ggtgccctcc aagtcagcga ctctctcgat    480
cagagcgcaa tcgtcgggga gctataacca ttgatactgc cagacggctg tgcaaggaag    540
ggcttccagt ggaagatgct tacttccatt cctgtgtctt tgatgtttta atttctggtg    600
atcccaactt taccgtggca gctcaggcag cactggagga tgcccgagcc ttcctgccag    660
acttagagaa gctgcatctc ttcccctcag atgctggggt tcctctttcc tcagcaaccc    720
tcttagctcc actcctttct gggctctttg ttctgtggct ttgcattcag taaggggacc    780
```

```
atcagtccca ttactagttt ggaaatgatt tggagataca gattggcata agaatgta      840 aagaatcatt aaaggaagca gggcctagga gacacgtgaa acaatgacat tatccagagt    900
cagatgaggc tgcagtccag ggttgaaatt atcacagaat aaggattctg gcaaggtta     960 ctgcattccg gatctctgtg gggctcttca ccaattttc cagcctcatt tatagtaaac    1020
aaattgttct aatccattta ctgcagattt caccttata agtttagagg tcatgaaggt    1080
tttaatgatc agtaaagatt taagggttga gattttaag aggcaagagc tgaaagcaga    1140
agacatgatc attagccata agaaactcaa aggaggaaga cataattagg gaaagaagtc    1200
tatttgatga atatgtgtgt gtaaggtatg ttctgctttc ttgattcaaa atgaagcag    1260 gcattgtcta gctcttaggt gaagggagtc tctgcttttg aagaatggca caggtaggac    1320
agaagtatca tccctacccc ctaactaatc tgttattaaa gctacaaatt cttcacacc    1379
```

<210> SEQ ID NO 7
<211> LENGTH: 1416
<212> TYPE: DNA
<213> ORGANISM: Artificial Sequence
<220> FEATURE:
<223> OTHER INFORMATION: Putative HFE2A cDNA from Homo sapiens

<400> SEQUENCE: 7

```
cttctctggt tccctgacct cagtgagaca gcagccggcc tggggacctg ggggagacac      60
ggaggacccc ctggctggag ctgacccaca gagtagggaa tcatggctgg agaattggat     120
agcagagtaa tgtttgacct ctggaaacac tcattctcaa tgcaagatcc tccgctgcaa     180
tgctgactca ccatcatatt taagaacatg caggaatgca ttgatcagaa ggtgtatcag     240
gctgaggtgg ataatcttcc tgtagccttt gaagatggtt ctatcaatgg aggtgaccga     300 cctggggat ccagtttgtc gattcaaact gctaaccctg gaaccatgt ggagatccaa       360 gctgcctaca ttggcacaac tataatcatt cggcagacag ctgggcagct ctccttctcc     420
atcaaggtag cagaggatgt ggccatggcc ttctcagctg aacaggacct gcagctctgt     480 gttgggggt gccctccaag tcagcgactc tctcgatcag agcgcaatcg tcggggagct      540
ataaccattg atactgccag acggctgtgc aaggaagggc ttccagtgga agatgcttac    600
ttccattcct gtgtctttga tgttttaatt tctggtgatc ccaactttac cgtggcagct    660
caggcagcac tggaggatgc ccgagccttc ctgccagact agagaagct gcatctcttc     720 ccctcagatg ctggggttcc tctttcctca gcaaccctct tagctccact cctttctggg     780
ctctttgttc tgtggctttg cattcagtaa ggggaccatc agtcccatta ctagtttgga    840
aatgatttgg agatacagat tggcatagaa gaatgtaaag aatcattaaa ggaagcaggg    900
cctaggagac acgtgaaaca atgacattat ccagagtcag atgaggctgc agtccagggt    960
tgaaattatc acagaataag gattctgggc aaggttactg cattccggat ctctgtgggg   1020
ctcttcacca ttttttccag cctcatttat agtaaacaaa ttgttctaat ccatttactg   1080
cagatttcac ccttataagt ttagaggtca tgaaggtttt aatgatcagt aaagatttaa   1140
gggttgagat tttaagagg caagagctga agcagaaga catgatcatt agccataaga    1200
aactcaaagg aggaagacat aattagggaa agaagtctat tgatgaata tgtgtgtgta    1260 aggtatgttc tgctttcttg attcaaaaat gaagcaggca ttgtctagct cttaggtgaa    1320
gggagtctct gcttttgaag aatggcacag gtaggacaga agtatcatcc ctacccccta    1380
actaatctgt tattaaagct acaaattctt cacacc                              1416
```

<210> SEQ ID NO 8
<211> LENGTH: 1939
<212> TYPE: DNA
<213> ORGANISM: Artificial Sequence
<220> FEATURE:
<223> OTHER INFORMATION: Putative HFE2A cDNA from Homo sapiens

<400> SEQUENCE: 8

| | | | | | |
|---|---|---|---|---|---|
| cttctctggt | tccctgacct | cagtgagaca | gcagccggcc | tggggacctg | ggggagacac | 60 |
| ggaggacccc | ctggctggag | ctgacccaca | gagtagggaa | tcatggctgg | agaattggat | 120 |
| agcagagtaa | tgtttgacct | ctggaaacac | tcattctcaa | tgcaagatcc | tccgctgcaa | 180 |
| tgctgagtac | gtatcgtcca | ctctgagcct | tagaggtggg | ggttcatcag | gagcacttcg | 240 |
| aggaggagga | ggaggaggcc | ggggtggagg | ggtgggctct | ggcggcctct | gtcgagccct | 300 |
| ccgctcctat | gcgctctgca | ctcggcgcac | cgcccgcacc | tgccgcgggg | acctcgcctt | 360 |
| ccattcggcg | gtacatggca | tcgaagacct | gatgatccag | cacaactgct | cccgccaggg | 420 |
| ccctacagcc | cctcccccgc | cccggggccc | cgccttcca | ggcgcgggct | ccggcctccc | 480 |
| tgccccggac | ccttgtgact | atgaaggccg | gttttcccgg | ctgcatggtc | gtccccccggg | 540 |
| gttcttgcat | gcgcttcct | tcggggaccc | ccatgtgcgc | agcttccacc | atcactttca | 600 |
| cacatgccgt | gtccaaggag | cttggcctct | actggataat | gacttcctct | ttgtccaagc | 660 |
| caccagctcc | cccatggcgt | tgggggccaa | cgctaccgcc | acccggaagc | tcaccatcat | 720 |
| atttaagaac | atgcaggaat | gcattgatca | gaaggtgtat | caggctgagg | tggataatct | 780 |
| tcctgtagcc | tttgaagatg | gttctatcaa | tggaggtgac | cgacctgggg | gatccagttt | 840 |
| gtcgattcaa | actgctaacc | ctgggaacca | tgtggagatc | caagctgcct | acattggcac | 900 |
| aactataatc | attcggcaga | cagctgggca | gctctccttc | tccatcaagg | tagcagagga | 960 |
| tgtggccatg | gccttctcag | ctgaacagga | cctgcagctc | tgtgttgggg | ggtgccctcc | 1020 |
| aagtcagcga | ctctctcgat | cagagcgcaa | tcgtcgggga | gctataacca | ttgatactgc | 1080 |
| cagacggctg | tgcaaggaag | ggcttccagt | ggaagatgct | tacttccatt | cctgtgtctt | 1140 |
| tgatgtttta | atttctggtg | atcccaactt | taccgtggca | gctcaggcag | cactggagga | 1200 |
| tgcccgagcc | ttcctgccag | acttagagaa | gctgcatctc | ttcccctcag | atgctggggt | 1260 |
| tcctcttttcc | tcagcaaccc | tcttagctcc | actccttctt | gggctctttg | ttctgtggct | 1320 |
| ttgcattcag | taaggggacc | atcagtccca | ttactagttt | ggaaatgatt | tggagataca | 1380 |
| gattggcata | gaagaatgta | agaatcatt | aaaggaagca | gggcctagga | gacacgtgaa | 1440 |
| acaatgacat | tatccagagt | cagatgaggc | tgcagtccag | ggttgaaatt | atcacagaat | 1500 |
| aaggattctg | gcaaggtta | ctgcattccg | gatctctgtg | gggctcttca | ccaattttc | 1560 |
| cagcctcatt | tatagtaaac | aaattgttct | aatccattta | ctgcagattt | cacccttata | 1620 |
| agtttagagg | tcatgaaggt | tttaatgatc | agtaaagatt | taagggttga | gattttaag | 1680 |
| aggcaagagc | tgaaagcaga | agacatgatc | attagccata | agaaactcaa | aggaggaaga | 1740 |
| cataattagg | gaaagaagtc | tatttgatga | atatgtgtgt | gtaaggtatg | ttctgcttc | 1800 |
| ttgattcaaa | aatgaagcag | gcattgtcta | gctcttaggt | gaagggagtc | tctgcttttg | 1860 |
| aagaatggca | caggtaggac | agaagtatca | tccctacccc | ctaactaatc | tgttattaaa | 1920 |
| gctacaaatt | cttcacacc | | | | | 1939 |

<210> SEQ ID NO 9
<211> LENGTH: 2143
<212> TYPE: DNA

<213> ORGANISM: Artificial Sequence
<220> FEATURE:
<223> OTHER INFORMATION: Putative HFE2A cDNA from Homo sapiens

<400> SEQUENCE: 9

```
cttctctggt tccctgacct cagtgagaca gcagccggcc tggggacctg ggggagacac      60
ggaggacccc ctggctggag ctgacccaca gagtagggaa tcatggctgg agaattggat     120
agcagagtaa tgtttgacct ctggaaacac caaatttctt ttttcagtca cttacagggc     180
ttccggtcaa aattcactag gtaggagggt catcagctgg aagaaccggc gcctgggaa      240
acctggctgg ataggtatgg gggagccagg ccagtcccct agtcccaggt cctcccatgg     300
cagtccccca actctaagca ctctcactct cctgctgctc ctctgtggac atgctcattc     360
tcaatgcaag atcctccgct gcaatgctga gtacgtatcg tccactctga gcttagagg      420
tgggggttca tcaggagcac ttcgaggagg aggaggagga ggccggggtg gaggggtggg     480
ctctggcggc ctctgtcgag ccctccgctc ctatgcgctc tgcactcggc gcaccgcccg     540
cacctgccgc ggggaccctcg ccttccattc ggcggtacat ggcatcgaag acctgatgat     600
ccagcacaac tgctcccgcc agggccctac agcccctccc ccgccccggg gccccgccct     660
tccaggcgcg ggctccggcc tccctgcccc ggaccttgt gactatgaag ccggtttttc     720
ccggctgcat ggtcgtcccc cggggttctt gcattgcgct tccttcgggg accccatgt      780
gcgcagcttc caccatcact ttcacacatg ccgtgtccaa ggagcttggc ctctactgga     840
taatgacttc ctctttgtcc aagccaccag ctcccccatg gcgttggggg ccaacgctac     900
cgccacccgg aagctcacca tcatatttaa gaacatgcag gaatgcattg atcagaaggt     960
gtatcaggct gaggtggata tcttcctgt agcctttgaa gatggttcta tcaatggagg    1020
tgaccgacct gggggatcca gtttgtcgat tcaaactgct aaccctggga accatgtgga    1080
gatccaagct gcctacattg cacaactat aatcattcgg cagacagctg ggcagctctc    1140
cttctccatc aaggtagcag aggatgtggc catggccttc tcagctgaac aggacctgca    1200
gctctgtgtt gggggggtgcc ctccaagtca gcgactctct cgatcagagc gcaatcgtcg    1260
gggagctata accattgata ctgccagacg gctgtgcaag gaagggcttc cagtggaaga    1320
tgcttacttc cattcctgtg tctttgatgt tttaatttct ggtgatccca acttaccgt      1380
ggcagctcag gcagcactgg aggatgcccg agccttcctg ccagacttag agaagctgca    1440
tctcttcccc tcagatgctg gggttcctct ttcctcagca accctcttag ctccactcct    1500
ttctgggctc tttgttctgt ggctttgcat tcagtaaggg gaccatcagt cccattacta    1560
gtttggaaat gatttggaga tacagattgg catagaagaa tgtaaagaat cattaaagga    1620
agcagggcct aggagacacg tgaaacaatg acattatcca gagtcagatg aggctgcagt    1680
ccagggttga aattatcaca gaataaggat tctgggcaag gttactgcat tccggatctc    1740
tgtgggctc ttcaccaatt tttccagcct catttatagt aaacaaattg ttctaatcca    1800
tttactgcag atttcaccct tataagttta gaggtcatga aggttttaat gatcagtaaa    1860
gatttaaggg ttgagatttt taagaggcaa gagctgaaag cagaagacat gatcattagc    1920
cataagaaac tcaaaggagg aagacataat tagggaaaga agtctatttg atgaatatgt    1980
gtgtgtaagg tatgttctgc tttcttgatt caaaaatgaa gcaggcattg tctagctctt    2040
aggtgaaggg agtctctgct tttgaagaat ggcacaggta ggacagaagt atcatcccta    2100
cccccctaact aatctgttat taaagctaca aattcttcac acc                      2143
```

-continued

```
<210> SEQ ID NO 10
<211> LENGTH: 200
<212> TYPE: PRT
<213> ORGANISM: Artificial Sequence
<220> FEATURE:
<223> OTHER INFORMATION: Potein 1 translation from HFE2A transcripts
      from Homo sapiens

<400> SEQUENCE: 10

Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg Gly Ala Ile
            100                 105                 110

Thr Ile Asp Thr Ala Arg Arg Leu Cys Lys Glu Gly Leu Pro Val Glu
        115                 120                 125

Asp Ala Tyr Phe His Ser Cys Val Phe Asp Val Leu Ile Ser Gly Asp
    130                 135                 140

Pro Asn Phe Thr Val Ala Ala Gln Ala Ala Leu Glu Asp Ala Arg Ala
145                 150                 155                 160

Phe Leu Pro Asp Leu Glu Lys Leu His Leu Phe Pro Ser Asp Ala Gly
                165                 170                 175

Val Pro Leu Ser Ser Ala Thr Leu Leu Ala Pro Leu Leu Ser Gly Leu
            180                 185                 190

Phe Val Leu Trp Leu Cys Ile Gln
        195                 200

<210> SEQ ID NO 11
<211> LENGTH: 313
<212> TYPE: PRT
<213> ORGANISM: Artificial Sequence
<220> FEATURE:
<223> OTHER INFORMATION: Potein 2 translation from HFE2A transcript
      from Homo sapiens

<400> SEQUENCE: 11

Met Ile Gln His Asn Cys Ser Arg Gln Gly Pro Thr Ala Pro Pro Pro
1               5                   10                  15

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
        35                  40                  45

Pro Gly Phe Leu His Cys Ala Ser Phe Gly Asp Pro His Val Arg Ser
    50                  55                  60

Phe His His His Phe His Thr Cys Arg Val Gln Gly Ala Trp Pro Leu
65                  70                  75                  80

Leu Asp Asn Asp Phe Leu Phe Val Gln Ala Thr Ser Ser Pro Met Ala
                85                  90                  95

Leu Gly Ala Asn Ala Thr Ala Thr Arg Lys Leu Thr Ile Ile Phe Lys
```

```
                100             105             110
Asn Met Gln Glu Cys Ile Asp Gln Lys Val Tyr Gln Ala Glu Val Asp
            115                 120                 125

Asn Leu Pro Val Ala Phe Glu Asp Gly Ser Ile Asn Gly Gly Asp Arg
        130                 135                 140

Pro Gly Gly Ser Ser Leu Ser Ile Gln Thr Ala Asn Pro Gly Asn His
145                 150                 155                 160

Val Glu Ile Gln Ala Ala Tyr Ile Gly Thr Thr Ile Ile Arg Gln
                165                 170                 175

Thr Ala Gly Gln Leu Ser Phe Ser Ile Lys Val Ala Glu Asp Val Ala
            180                 185                 190

Met Ala Phe Ser Ala Glu Gln Asp Leu Gln Leu Cys Val Gly Gly Cys
            195                 200                 205

Pro Pro Ser Gln Arg Leu Ser Arg Ser Glu Arg Asn Arg Gly Ala
210                 215                 220

Ile Thr Ile Asp Thr Ala Arg Arg Leu Cys Lys Glu Gly Leu Pro Val
225                 230                 235                 240

Glu Asp Ala Tyr Phe His Ser Cys Val Phe Asp Val Leu Ile Ser Gly
                245                 250                 255

Asp Pro Asn Phe Thr Val Ala Ala Gln Ala Ala Leu Glu Asp Ala Arg
            260                 265                 270

Ala Phe Leu Pro Asp Leu Glu Lys Leu His Leu Phe Pro Ser Asp Ala
            275                 280                 285

Gly Val Pro Leu Ser Ser Ala Thr Leu Leu Ala Pro Leu Leu Ser Gly
            290                 295                 300

Leu Phe Val Leu Trp Leu Cys Ile Gln
305                 310

<210> SEQ ID NO 12
<211> LENGTH: 426
<212> TYPE: PRT
<213> ORGANISM: Artificial Sequence
<220> FEATURE:
<223> OTHER INFORMATION: Potein 3 translation from HFE2A transcript
      from Homo sapiens

<400> SEQUENCE: 12

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly
    50                  55                  60

Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
        130                 135                 140
```

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 13
<211> LENGTH: 35
<212> TYPE: PRT
<213> ORGANISM: Artificial Sequence
<220> FEATURE:
<223> OTHER INFORMATION: N-terminal signal peptide from Protein 3 from
      Homo sapiens

<400> SEQUENCE: 13

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
            20                  25                  30

Ala His Ser
        35

<210> SEQ ID NO 14
<211> LENGTH: 391
<212> TYPE: PRT
<213> ORGANISM: Artificial Sequence

```
<220> FEATURE:
<223> OTHER INFORMATION: C-terminal signal peptide from Protein 3 from
      Homo sapiens

<400> SEQUENCE: 14

Gln Cys Lys Ile Leu Arg Cys Asn Ala Glu Tyr Val Ser Ser Thr Leu
1               5                   10                  15

Ser Leu Arg Gly Gly Gly Ser Ser Gly Ala Leu Arg Gly Gly Gly Gly
            20                  25                  30

Gly Gly Arg Gly Gly Gly Val Gly Ser Gly Gly Leu Cys Arg Ala Leu
        35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
        115                 120                 125

Phe Leu His Cys Ala Ser Phe Gly Asp Pro His Val Arg Ser Phe His
130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
        195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
225                 230                 235                 240

Ile Gln Ala Ala Tyr Ile Gly Thr Thr Ile Ile Ile Arg Gln Thr Ala
                245                 250                 255

Gly Gln Leu Ser Phe Ser Ile Lys Val Ala Glu Asp Val Ala Met Ala
            260                 265                 270

Phe Ser Ala Glu Gln Asp Leu Gln Leu Cys Val Gly Gly Cys Pro Pro
        275                 280                 285

Ser Gln Arg Leu Ser Arg Ser Glu Arg Asn Arg Arg Gly Ala Ile Thr
    290                 295                 300

Ile Asp Thr Ala Arg Arg Leu Cys Lys Glu Gly Leu Pro Val Glu Asp
305                 310                 315                 320

Ala Tyr Phe His Ser Cys Val Phe Asp Val Leu Ile Ser Gly Asp Pro
                325                 330                 335

Asn Phe Thr Val Ala Ala Gln Ala Ala Leu Glu Asp Ala Arg Ala Phe
            340                 345                 350

Leu Pro Asp Leu Glu Lys Leu His Leu Phe Pro Ser Asp Ala Gly Val
        355                 360                 365

Pro Leu Ser Ser Ala Thr Leu Leu Ala Pro Leu Leu Ser Gly Leu Phe
    370                 375                 380

Val Leu Trp Leu Cys Ile Gln
```

-continued

```
385                390

<210> SEQ ID NO 15
<211> LENGTH: 172
<212> TYPE: PRT
<213> ORGANISM: Artificial Sequence
<220> FEATURE:
<223> OTHER INFORMATION: N-terminal Asp/Pro peptide from Protein 3 from
      Homo sapiens

<400> SEQUENCE: 15

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Ser Ser Gly Ala Leu Arg Gly
    50                  55                  60

Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
        115                 120                 125

Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp
                165                 170

<210> SEQ ID NO 16
<211> LENGTH: 137
<212> TYPE: PRT
<213> ORGANISM: Artificial Sequence
<220> FEATURE:
<223> OTHER INFORMATION: N-terminal Asp/Pro peptide from Protein 3 from
      Homo sapiens

<400> SEQUENCE: 16

Gln Cys Lys Ile Leu Arg Cys Asn Ala Glu Tyr Val Ser Ser Thr Leu
1               5                   10                  15

Ser Leu Arg Gly Gly Gly Ser Ser Gly Ala Leu Arg Gly Gly Gly Gly
            20                  25                  30

Gly Gly Arg Gly Gly Gly Val Gly Ser Gly Gly Leu Cys Arg Ala Leu
        35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
```

```
                115                 120                 125
Phe Leu His Cys Ala Ser Phe Gly Asp
    130                 135

<210> SEQ ID NO 17
<211> LENGTH: 254
<212> TYPE: PRT
<213> ORGANISM: Artificial Sequence
<220> FEATURE:
<223> OTHER INFORMATION: C-terminal Asp/Pro peptide from Protein 3 from
      Homo sapiens

<400> SEQUENCE: 17

Pro His Val Arg Ser Phe His His Phe His Thr Cys Arg Val Gln
1               5                   10                  15

Gly Ala Trp Pro Leu Leu Asp Asn Asp Phe Leu Phe Val Gln Ala Thr
            20                  25                  30

Ser Ser Pro Met Ala Leu Gly Ala Asn Ala Thr Ala Thr Arg Lys Leu
        35                  40                  45

Thr Ile Ile Phe Lys Asn Met Gln Glu Cys Ile Asp Gln Lys Val Tyr
    50                  55                  60

Gln Ala Glu Val Asp Asn Leu Pro Val Ala Phe Glu Asp Gly Ser Ile
65                  70                  75                  80

Asn Gly Gly Asp Arg Pro Gly Gly Ser Ser Leu Ser Ile Gln Thr Ala
                85                  90                  95

Asn Pro Gly Asn His Val Glu Ile Gln Ala Ala Tyr Ile Gly Thr Thr
            100                 105                 110

Ile Ile Ile Arg Gln Thr Ala Gly Gln Leu Ser Phe Ser Ile Lys Val
        115                 120                 125

Ala Glu Asp Val Ala Met Ala Phe Ser Ala Glu Gln Asp Leu Gln Leu
    130                 135                 140

Cys Val Gly Gly Cys Pro Pro Ser Gln Arg Leu Ser Arg Ser Glu Arg
145                 150                 155                 160

Asn Arg Arg Gly Ala Ile Thr Ile Asp Thr Ala Arg Arg Leu Cys Lys
                165                 170                 175

Glu Gly Leu Pro Val Glu Asp Ala Tyr Phe His Ser Cys Val Phe Asp
            180                 185                 190

Val Leu Ile Ser Gly Asp Pro Asn Phe Thr Val Ala Ala Gln Ala Ala
        195                 200                 205

Leu Glu Asp Ala Arg Ala Phe Leu Pro Asp Leu Glu Lys Leu His Leu
    210                 215                 220

Phe Pro Ser Asp Ala Gly Val Pro Leu Ser Ser Ala Thr Leu Leu Ala
225                 230                 235                 240

Pro Leu Leu Ser Gly Leu Phe Val Leu Trp Leu Cys Ile Gln
                245                 250

<210> SEQ ID NO 18
<211> LENGTH: 335
<212> TYPE: PRT
<213> ORGANISM: Artificial Sequence
<220> FEATURE:
<223> OTHER INFORMATION: N-terminal Furin peptide from Protein 3 from
      Homo sapiens

<400> SEQUENCE: 18

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
```

```
                    20                  25                  30
Ala His Ser Gln Cys Lys Ile Leu Arg Cys Asn Ala Glu Tyr Val Ser
             35                  40                  45

Ser Thr Leu Ser Leu Arg Gly Gly Ser Ser Gly Ala Leu Arg Gly
 50                  55                  60

Gly Gly Gly Gly Arg Gly Gly Val Gly Ser Gly Gly Leu Cys
 65                  70                  75                  80

Arg Ala Leu Arg Ser Tyr Ala Leu Cys Thr Arg Thr Ala Arg Thr
                 85                  90                  95

Cys Arg Gly Asp Leu Ala Phe His Ser Ala Val His Gly Ile Glu Asp
                100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
                180                 185                 190

Leu Leu Asp Asn Asp Phe Leu Phe Val Gln Ala Thr Ser Ser Pro Met
            195                 200                 205

Ala Leu Gly Ala Asn Ala Thr Ala Thr Arg Lys Leu Thr Ile Ile Phe
210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
                260                 265                 270

His Val Glu Ile Gln Ala Ala Tyr Ile Gly Thr Thr Ile Ile Ile Arg
            275                 280                 285

Gln Thr Ala Gly Gln Leu Ser Phe Ser Ile Lys Val Ala Glu Asp Val
290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg
                325                 330                 335

<210> SEQ ID NO 19
<211> LENGTH: 163
<212> TYPE: PRT
<213> ORGANISM: Artificial Sequence
<220> FEATURE:
<223> OTHER INFORMATION: Asp/Pro to Furin peptide from Protein 3 from
      Homo sapiens

<400> SEQUENCE: 19

Pro His Val Arg Ser Phe His His His Phe His Thr Cys Arg Val Gln
1               5                   10                  15

Gly Ala Trp Pro Leu Leu Asp Asn Asp Phe Leu Phe Val Gln Ala Thr
                20                  25                  30

Ser

```
Thr Ile Ile Phe Lys Asn Met Gln Glu Cys Ile Asp Gln Lys Val Tyr
    50                  55                  60

Gln Ala Glu Val Asp Asn Leu Pro Val Ala Phe Glu Asp Gly Ser Ile
 65                  70                  75                  80

Asn Gly Gly Asp Arg Pro Gly Gly Ser Ser Leu Ser Ile Gln Thr Ala
                 85                  90                  95

Asn Pro Gly Asn His Val Glu Ile Gln Ala Ala Tyr Ile Gly Thr Thr
                100                 105                 110

Ile Ile Ile Arg Gln Thr Ala Gly Gln Leu Ser Phe Ser Ile Lys Val
            115                 120                 125

Ala Glu Asp Val Ala Met Ala Phe Ser Ala Glu Gln Asp Leu Gln Leu
        130                 135                 140

Cys Val Gly Gly Cys Pro Pro Ser Gln Arg Leu Ser Arg Ser Glu Arg
145                 150                 155                 160

Asn Arg Arg

<210> SEQ ID NO 20
<211> LENGTH: 91
<212> TYPE: PRT
<213> ORGANISM: Artificial Sequence
<220> FEATURE:
<223> OTHER INFORMATION: C-terminal Furin peptide from Protein 3 from
      Homo sapiens

<400> SEQUENCE: 20

Gly Ala Ile Thr Ile Asp Thr Ala Arg Arg Leu Cys Lys Glu Gly Leu
1               5                   10                  15

Pro Val Glu Asp Ala Tyr Phe His Ser Cys Val Phe Asp Val Leu Ile
                20                  25                  30

Ser Gly Asp Pro Asn Phe Thr Val Ala Ala Gln Ala Ala Leu Glu Asp
            35                  40                  45

Ala Arg Ala Phe Leu Pro Asp Leu Glu Lys Leu His Leu Phe Pro Ser
        50                  55                  60

Asp Ala Gly Val Pro Leu Ser Ser Ala Thr Leu Leu Ala Pro Leu Leu
65                  70                  75                  80

Ser Gly Leu Phe Val Leu Trp Leu Cys Ile Gln
                85                  90

<210> SEQ ID NO 21
<211> LENGTH: 26
<212> TYPE: PRT
<213> ORGANISM: Artificial Sequence
<220> FEATURE:
<223> OTHER INFORMATION: C-terminal GPI peptide from Protein 3 from
      Homo sapiens

<400> SEQUENCE: 21

Ala Gly Val Pro Leu Ser Ser Ala Thr Leu Leu Ala Pro Leu Leu Ser
1               5                   10                  15

Gly Leu Phe Val Leu Trp Leu Cys Ile Gln
                20                  25

<210> SEQ ID NO 22
<211> LENGTH: 400
<212> TYPE: PRT
<213> ORGANISM: Artificial Sequence
<220> FEATURE:
<223> OTHER INFORMATION: N-terminal GPI anchor peptide from Protein 3
      from Homo sapiens

<400> SEQUENCE: 22
```

```
Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His
        20                  25                  30

Ala His Ser Gln Cys Lys Ile Leu Arg Cys Asn Ala Glu Tyr Val Ser
            35                  40                  45

Ser Thr Leu Ser Leu Arg Gly Gly Ser Gly Ala Leu Arg Gly
    50                  55                  60

Gly Gly Gly Gly Arg Gly Gly Val Gly Ser Gly Gly Leu Cys
65              70                  75                  80

Arg Ala Leu Arg Ser Tyr Ala Leu Cys Thr Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
            115                 120                 125

Pro Pro Arg Gly Pro Ala Leu Pro Gly Ala Gly Ser Gly Leu Pro Ala
        130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
            195                 200                 205

Ala Leu Gly Ala Asn Ala Thr Ala Thr Arg Lys Leu Thr Ile Ile Phe
        210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Arg
            275                 280                 285

Gln Thr Ala Gly Gln Leu Ser Phe Ser Ile Lys Val Ala Glu Asp Val
        290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
            355                 360                 365

Gly Asp Pro Asn Phe Thr Val Ala Ala Gln Ala Ala Leu Glu Asp Ala
        370                 375                 380

Arg Ala Phe Leu Pro Asp Leu Glu Lys Leu His Leu Phe Pro Ser Asp
385                 390                 395                 400

<210> SEQ ID NO 23
<211> LENGTH: 65
```

```
<212> TYPE: PRT
<213> ORGANISM: Artificial Sequence
<220> FEATURE:
<223> OTHER INFORMATION: Furin to GPI anchor peptide from Protein 3 from
      Homo sapiens

<400> SEQUENCE: 23

Gly Ala Ile Thr Ile Asp Thr Ala Arg Arg Leu Cys Lys Glu Gly Leu
1               5                   10                  15

Pro Val Glu Asp Ala Tyr Phe His Ser Cys Val Phe Asp Val Leu Ile
                20                  25                  30

Ser Gly Asp Pro Asn Phe Thr Val Ala Ala Gln Ala Ala Leu Glu Asp
            35                  40                  45

Ala Arg Ala Phe Leu Pro Asp Leu Glu Lys Leu His Leu Phe Pro Ser
        50                  55                  60

Asp
65

<210> SEQ ID NO 24
<211> LENGTH: 228
<212> TYPE: PRT
<213> ORGANISM: Artificial Sequence
<220> FEATURE:
<223> OTHER INFORMATION: Asp/Pro to GPI peptide from Protein 3 from
      Homo sapiens

<400> SEQUENCE: 24

Pro His Val Arg Ser Phe His His His Phe His Thr Cys Arg Val Gln
1               5                   10                  15

Gly Ala Trp Pro Leu Leu Asp Asn Asp Phe Leu Phe Val Gln Ala Thr
                20                  25                  30

Ser Ser Pro Met Ala Leu Gly Ala Asn Ala Thr Ala Thr Arg Lys Leu
            35                  40                  45

Thr Ile Ile Phe Lys Asn Met Gln Glu Cys Ile Asp Gln Lys Val Tyr
        50                  55                  60

Gln Ala Glu Val Asp Asn Leu Pro Val Ala Phe Glu Asp Gly Ser Ile
65                  70                  75                  80

Asn Gly Gly Asp Arg Pro Gly Gly Ser Ser Leu Ser Ile Gln Thr Ala
                85                  90                  95

Asn Pro Gly Asn His Val Glu Ile Gln Ala Ala Tyr Ile Gly Thr Thr
            100                 105                 110

Ile Ile Ile Arg Gln Thr Ala Gly Gln Leu Ser Phe Ser Ile Lys Val
        115                 120                 125

Ala Glu Asp Val Ala Met Ala Phe Ser Ala Glu Gln Asp Leu Gln Leu
130                 135                 140

Cys Val Gly Gly Cys Pro Pro Ser Gln Arg Leu Ser Arg Ser Glu Arg
145                 150                 155                 160

Asn Arg Arg Gly Ala Ile Thr Ile Asp Thr Ala Arg Arg Leu Cys Lys
                165                 170                 175

Glu Gly Leu Pro Val Glu Asp Ala Tyr Phe His Ser Cys Val Phe Asp
            180                 185                 190

Val Leu Ile Ser Gly Asp Pro Asn Phe Thr Val Ala Ala Gln Ala Ala
        195                 200                 205

Leu Glu Asp Ala Arg Ala Phe Leu Pro Asp Leu Glu Lys Leu His Leu
210                 215                 220

Phe Pro Ser Asp
225
```

<210> SEQ ID NO 25
<211> LENGTH: 365
<212> TYPE: PRT
<213> ORGANISM: Artificial Sequence
<220> FEATURE:
<223> OTHER INFORMATION: Signal to GPI anchor peptide from Protein 3
      from Homo sapiens

<400> SEQUENCE: 25

```
Gln Cys Lys Ile Leu Arg Cys Asn Ala Glu Tyr Val Ser Ser Thr Leu
1               5                   10                  15

Ser Leu Arg Gly Gly Ser Ser Gly Ala Leu Arg Gly Gly Gly Gly Gly
            20                  25                  30

Gly Gly Arg Gly Gly Gly Val Gly Ser Gly Gly Leu Cys Arg Ala Leu
        35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
        115                 120                 125

Phe Leu His Cys Ala Ser Phe Gly Asp Pro His Val Arg Ser Phe His
    130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
        195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
225                 230                 235                 240

Ile Gln Ala Ala Tyr Ile Gly Thr Thr Ile Ile Arg Gln Thr Ala
                245                 250                 255

Gly Gln Leu Ser Phe Ser Ile Lys Val Ala Glu Asp Val Ala Met Ala
            260                 265                 270

Phe Ser Ala Glu Gln Asp Leu Gln Leu Cys Val Gly Gly Cys Pro Pro
        275                 280                 285

Ser Gln Arg Leu Ser Arg Ser Glu Arg Asn Arg Arg Gly Ala Ile Thr
    290                 295                 300

Ile Asp Thr Ala Arg Arg Leu Cys Lys Glu Gly Leu Pro Val Glu Asp
305                 310                 315                 320

Ala Tyr Phe His Ser Cys Val Phe Asp Val Leu Ile Ser Gly Asp Pro
                325                 330                 335

Asn Phe Thr Val Ala Ala Gln Ala Ala Leu Glu Asp Ala Arg Ala Phe
            340                 345                 350

Leu Pro Asp Leu Glu Lys Leu His Leu Phe Pro Ser Asp
        355                 360                 365
```

<210> SEQ ID NO 26
<211> LENGTH: 300
<212> TYPE: PRT
<213> ORGANISM: Artificial Sequence
<220> FEATURE:
<223> OTHER INFORMATION: Signal to Furin peptide from Protein 3 from
    Homo sapiens

<400> SEQUENCE: 26

```
Gln Cys Lys Ile Leu Arg Cys Asn Ala Glu Tyr Val Ser Ser Thr Leu
1               5                   10                  15

Ser Leu Arg Gly Gly Ser Ser Gly Ala Leu Arg Gly Gly Gly
            20                  25                  30

Gly Gly Arg Gly Gly Val Gly Ser Gly Leu Cys Arg Ala Leu
                35                  40                  45

Arg Ser Tyr Ala Leu Cys Thr Arg Arg Thr Ala Arg Thr Cys Arg Gly
    50                  55                  60

Asp Leu Ala Phe His Ser Ala Val His Gly Ile Glu Asp Leu Met Ile
65                  70                  75                  80

Gln His Asn Cys Ser Arg Gln Gly Pro Thr Ala Pro Pro Pro Pro Arg
                85                  90                  95

Gly Pro Ala Leu Pro Gly Ala Gly Ser Gly Leu Pro Ala Pro Asp Pro
            100                 105                 110

Cys Asp Tyr Glu Gly Arg Phe Ser Arg Leu His Gly Arg Pro Pro Gly
            115                 120                 125

Phe Leu His Cys Ala Ser Phe Gly Asp Pro His Val Arg Ser Phe His
    130                 135                 140

His His Phe His Thr Cys Arg Val Gln Gly Ala Trp Pro Leu Leu Asp
145                 150                 155                 160

Asn Asp Phe Leu Phe Val Gln Ala Thr Ser Ser Pro Met Ala Leu Gly
                165                 170                 175

Ala Asn Ala Thr Ala Thr Arg Lys Leu Thr Ile Ile Phe Lys Asn Met
            180                 185                 190

Gln Glu Cys Ile Asp Gln Lys Val Tyr Gln Ala Glu Val Asp Asn Leu
            195                 200                 205

Pro Val Ala Phe Glu Asp Gly Ser Ile Asn Gly Gly Asp Arg Pro Gly
    210                 215                 220

Gly Ser Ser Leu Ser Ile Gln Thr Ala Asn Pro Gly Asn His Val Glu
225                 230                 235                 240

Ile Gln Ala Ala Tyr Ile Gly Thr Thr Ile Ile Arg Gln Thr Ala
                245                 250                 255

Gly Gln Leu Ser Phe Ser Ile Lys Val Ala Glu Asp Val Ala Met Ala
            260                 265                 270

Phe Ser Ala Glu Gln Asp Leu Gln Leu Cys Val Gly Gly Cys Pro Pro
    275                 280                 285

Ser Gln Arg Leu Ser Arg Ser Glu Arg Asn Arg Arg
    290                 295                 300
```

<210> SEQ ID NO 27
<211> LENGTH: 109
<212> TYPE: PRT
<213> ORGANISM: Artificial Sequence
<220> FEATURE:
<223> OTHER INFORMATION: N-terminal Furin peptide from Protein 1 from
    Homo sapiens

<400> SEQUENCE: 27

```
Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg
            100                 105
```

<210> SEQ ID NO 28
<211> LENGTH: 174
<212> TYPE: PRT
<213> ORGANISM: Artificial Sequence
<220> FEATURE:
<223> OTHER INFORMATION: N-terminal GPI anchor peptide from Protein 1
      from Homo sapiens

<400> SEQUENCE: 28

```
Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg Gly Ala Ile
            100                 105                 110

Thr Ile Asp Thr Ala Arg Arg Leu Cys Lys Glu Gly Leu Pro Val Glu
        115                 120                 125

Asp Ala Tyr Phe His Ser Cys Val Phe Asp Val Leu Ile Ser Gly Asp
    130                 135                 140

Pro Asn Phe Thr Val Ala Ala Gln Ala Ala Leu Glu Asp Ala Arg Ala
145                 150                 155                 160

Phe Leu Pro Asp Leu Glu Lys Leu His Leu Phe Pro Ser Asp
            165                 170
```

<210> SEQ ID NO 29
<211> LENGTH: 59
<212> TYPE: PRT
<213> ORGANISM: Artificial Sequence
<220> FEATURE:
<223> OTHER INFORMATION: N-terminal Asp/Pro peptide from Protein 2 from
      Homo sapiens

<400> SEQUENCE: 29

```
Met Ile Gln His Asn Cys Ser Arg Gln Gly Pro Thr Ala Pro Pro Pro
1               5                   10                  15
```

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
        35                  40                  45

Pro Gly Phe Leu His Cys Ala Ser Phe Gly Asp
    50                  55

<210> SEQ ID NO 30
<211> LENGTH: 222
<212> TYPE: PRT
<213> ORGANISM: Artificial Sequence
<220> FEATURE:
<223> OTHER INFORMATION: N-terminal Furin peptide from Protein 2 from
      Homo sapiens

<400> SEQUENCE: 30

Met Ile Gln His Asn Cys Ser Arg Gln Gly Pro Thr Ala Pro Pro Pro
1               5                   10                  15

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
        35                  40                  45

Pro Gly Phe Leu His Cys Ala Ser Phe Gly Asp Pro His Val Arg Ser
    50                  55                  60

Phe His His His Phe His Thr Cys Arg Val Gln Gly Ala Trp Pro Leu
65                  70                  75                  80

Leu Asp Asn Asp Phe Leu Phe Val Gln Ala Thr Ser Ser Pro Met Ala
                85                  90                  95

Leu Gly Ala Asn Ala Thr Ala Thr Arg Lys Leu Thr Ile Ile Phe Lys
            100                 105                 110

Asn Met Gln Glu Cys Ile Asp Gln Lys Val Tyr Gln Ala Glu Val Asp
        115                 120                 125

Asn Leu Pro Val Ala Phe Glu Asp Gly Ser Ile Asn Gly Gly Asp Arg
    130                 135                 140

Pro Gly Gly Ser Ser Leu Ser Ile Gln Thr Ala Asn Pro Gly Asn His
145                 150                 155                 160

Val Glu Ile Gln Ala Ala Tyr Ile Gly Thr Thr Ile Ile Arg Gln
                165                 170                 175

Thr Ala Gly Gln Leu Ser Phe Ser Ile Lys Val Ala Glu Asp Val Ala
            180                 185                 190

Met Ala Phe Ser Ala Glu Gln Asp Leu Gln Leu Cys Val Gly Gly Cys
        195                 200                 205

Pro Pro Ser Gln Arg Leu Ser Arg Ser Glu Arg Asn Arg Arg
    210                 215                 220

<210> SEQ ID NO 31
<211> LENGTH: 287
<212> TYPE: PRT
<213> ORGANISM: Artificial Sequence
<220> FEATURE:
<223> OTHER INFORMATION: N-terminal GPI anchor peptide from Protein 2
      from Homo sapiens

<400> SEQUENCE: 31

Met Ile Gln His Asn Cys Ser Arg Gln Gly Pro Thr Ala Pro Pro Pro
1               5                   10                  15

Pro Arg Gly Pro Ala Leu Pro Gly Ala Gly Ser Gly Leu Pro Ala Pro
            20                  25                  30

-continued

```
Asp Pro Cys Asp Tyr Glu Gly Arg Phe Ser Arg Leu His Gly Arg Pro
         35                  40                  45

Pro Gly Phe Leu His Cys Ala Ser Phe Gly Asp Pro His Val Arg Ser
 50                  55                  60

Phe His His His Phe His Thr Cys Arg Val Gln Gly Ala Trp Pro Leu
 65                  70                  75                  80

Leu Asp Asn Asp Phe Leu Phe Val Gln Ala Thr Ser Ser Pro Met Ala
                 85                  90                  95

Leu Gly Ala Asn Ala Thr Ala Thr Arg Lys Leu Thr Ile Ile Phe Lys
            100                 105                 110

Asn Met Gln Glu Cys Ile Asp Gln Lys Val Tyr Gln Ala Glu Val Asp
        115                 120                 125

Asn Leu Pro Val Ala Phe Glu Asp Gly Ser Ile Asn Gly Gly Asp Arg
    130                 135                 140

Pro Gly Gly Ser Ser Leu Ser Ile Gln Thr Ala Asn Pro Gly Asn His
145                 150                 155                 160

Val Glu Ile Gln Ala Ala Tyr Ile Gly Thr Thr Ile Ile Arg Gln
                165                 170                 175

Thr Ala Gly Gln Leu Ser Phe Ser Ile Lys Val Ala Glu Asp Val Ala
            180                 185                 190

Met Ala Phe Ser Ala Glu Gln Asp Leu Gln Leu Cys Val Gly Gly Cys
        195                 200                 205

Pro Pro Ser Gln Arg Leu Ser Arg Ser Glu Arg Asn Arg Arg Gly Ala
    210                 215                 220

Ile Thr Ile Asp Thr Ala Arg Arg Leu Cys Lys Glu Gly Leu Pro Val
225                 230                 235                 240

Glu Asp Ala Tyr Phe His Ser Cys Val Phe Asp Val Leu Ile Ser Gly
                245                 250                 255

Asp Pro Asn Phe Thr Val Ala Ala Gln Ala Ala Leu Glu Asp Ala Arg
            260                 265                 270

Ala Phe Leu Pro Asp Leu Glu Lys Leu His Leu Phe Pro Ser Asp
        275                 280                 285

<210> SEQ ID NO 32
<211> LENGTH: 21
<212> TYPE: DNA
<213> ORGANISM: Artificial
<220> FEATURE:
<223> OTHER INFORMATION: Oligonucleotide showing wild type sequence of
      HFE2A from Homo sapiens

<400> SEQUENCE: 32
gtccaaggag attggcctct a                                              21

<210> SEQ ID NO 33
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 33
gcctgggaaa cctggctgga t                                              21

<210> SEQ ID NO 34
<211> LENGTH: 21
<212> TYPE: DNA
```

<213> ORGANISM: Artificial
<220> FEATURE:
<223> OTHER INFORMATION: Oligonucleotide showing wild type sequence of
     HFE2A from Homo sapiens

<400> SEQUENCE: 34
gcctgggaaa gctggctgga t                                              21

<210> SEQ ID NO 35
<211> LENGTH: 21
<212> TYPE: DNA
<213> ORGANISM: Artificial
<220> FEATURE:
<223> OTHER INFORMATION: Oligonucleotide showing mutant sequence of
     HFE2A from Homo sapiens

<400> SEQUENCE: 35
tcccttctgt ctttagctca t                                              21

<210> SEQ ID NO 36
<211> LENGTH: 21
<212> TYPE: DNA
<213> ORGANISM: Artificial
<220> FEATURE:
<223> OTHER INFORMATION: Oligonucleotide showing wild type sequence
     of HFE2A from Homo sapiens

<400> SEQUENCE: 36
tcccttctgt gtttagctca t                                              21

<210> SEQ ID NO 37
<211> LENGTH: 20
<212> TYPE: DNA
<213> ORGANISM: Artificial
<220> FEATURE:
<223> OTHER INFORMATION: Oligonucleotide showing mutant sequence of
     HFE2A from Homo sapiens

<400> SEQUENCE: 37
gaggaggagg ccggggtgga                                                20

<210> SEQ ID NO 38
<211> LENGTH: 23
<212> TYPE: DNA
<213> ORGANISM: Artificial
<220> FEATURE:
<223> OTHER INFORMATION: Oligonucleotide showing wild type sequence
     of HFE2A from Homo sapiens

<400> SEQUENCE: 38
gaggaggagg aggccggggt gga                                            23

<210> SEQ ID NO 39
<211> LENGTH: 21
<212> TYPE: DNA
<213> ORGANISM: Artificial
<220> FEATURE:
<223> OTHER INFORMATION: Oligonucleotide showing mutant sequence of
     HFE2A from Homo sapiens

<400> SEQUENCE: 39
gcctccctgc cccggaccct t                                              21

<210> SEQ ID NO 40
<211> LENGTH: 21
<212> TYPE: DNA
<213> ORGANISM: Artificial

```
<220> FEATURE:
<223> OTHER INFORMATION: Oligonucleotide showing wild type sequence
      of HFE2A from Homo sapiens

<400> SEQUENCE: 40
gcctccctgc gccggaccct t                                              21

<210> SEQ ID NO 41
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 41
atggtcgtcc cccggggttc t                                              21

<210> SEQ ID NO 42
<211> LENGTH: 21
<212> TYPE: DNA
<213> ORGANISM: Artificial
<220> FEATURE:
<223> OTHER INFORMATION: Oligonucleotide showing wild type sequence
      of HFE2A from Homo sapiens

<400> SEQUENCE: 42
atggtcgtcc accggggttc t                                              21

<210> SEQ ID NO 43
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 43
cgtcccccgg ggttcttgca t                                              21

<210> SEQ ID NO 44
<211> LENGTH: 21
<212> TYPE: DNA
<213> ORGANISM: Artificial
<220> FEATURE:
<223> OTHER INFORMATION: Oligonucleotide showing wild type sequence
      of HFE2A from Homo sapiens

<400> SEQUENCE: 44
cgtcccccgg cgttcttgca t                                              21

<210> SEQ ID NO 45
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 45
gtccaaggag cttggcctct a                                              21

<210> SEQ ID NO 46
<211> LENGTH: 21
<212> TYPE: DNA
<213> ORGANISM: Artificial
<220> FEATURE:
```

```
<223> OTHER INFORMATION: Oligonucleotide showing wild type sequence
      of HFE2A from Homo sapiens

<400> SEQUENCE: 46
gtccaaggag attggcctct a                                              21

<210> SEQ ID NO 47
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 47
cccccatggc gttgggggcc a                                              21

<210> SEQ ID NO 48
<211> LENGTH: 21
<212> TYPE: DNA
<213> ORGANISM: Artificial
<220> FEATURE:
<223> OTHER INFORMATION: Oligonucleotide showing wild type sequence
      of HFE2A from Homo sapiens

<400> SEQUENCE: 48
cccccatggc tttgggggcc a                                              21

<210> SEQ ID NO 49
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 49
taagaacatg caggaatgca t                                              21

<210> SEQ ID NO 50
<211> LENGTH: 21
<212> TYPE: DNA
<213> ORGANISM: Artificial
<220> FEATURE:
<223> OTHER INFORMATION: Oligonucleotide showing wild type sequence
      of HFE2A from Homo sapiens

<400> SEQUENCE: 50
taagaacatg aaggaatgca t                                              21

<210> SEQ ID NO 51
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 51
gccttctcag ctgaacagga c                                              21

<210> SEQ ID NO 52
<211> LENGTH: 21
<212> TYPE: DNA
<213> ORGANISM: Artificial
<220> FEATURE:
<223> OTHER INFORMATION: Oligonucleotide showing wild type sequence
```

```
                         of HFE2A from Homo sapiens

<400> SEQUENCE: 52
gccttctcag gtgaacagga c                                              21

<210> SEQ ID NO 53
<211> LENGTH: 21
<212> TYPE: DNA
<213> ORGANISM: Artificial
<220> FEATURE:
<223> OTHER INFORMATION: Oligonucleotide showing mutant sequence of
      HFE2A from Homo sapiens

<400> SEQUENCE: 53
agatgctggg gttcctcttt c                                              21
```